(12) United States Patent
Freeman

(10) Patent No.: US 7,364,565 B2
(45) Date of Patent: Apr. 29, 2008

(54) CONTROLLED ENZYMATIC REMOVAL AND RETRIEVAL OF CELLS

(75) Inventor: Amihay Freeman, Ben Shemen (IL)

(73) Assignee: Ramot at Tel Aviv University Ltd., Tel Aviv (IL)

( * ) Notice: Subject to any disclaimer, the term of this patent is extended or adjusted under 35 U.S.C. 154(b) by 308 days.

(21) Appl. No.: 10/768,749

(22) Filed: Jan. 27, 2004

(65) Prior Publication Data

US 2004/0186421 A1    Sep. 23, 2004

Related U.S. Application Data

(63) Continuation-in-part of application No. PCT/IL02/00572, filed on Jul. 16, 2002.

(51) Int. Cl.
*A61N 1/30* (2006.01)
(52) U.S. Cl. .................................................. 604/19
(58) Field of Classification Search ................ 604/289, 604/297, 290, 311, 312, 313, 35, 36, 23, 19; 607/160, 162, 159
See application file for complete search history.

(56) References Cited

U.S. PATENT DOCUMENTS

| | | | | |
|---|---|---|---|---|
| 191,775 A | * | 6/1877 | Parsons | 604/40 |
| 551,973 A | * | 12/1895 | Knap | 604/40 |
| 1,138,346 A | | 5/1915 | Bacon | 122/114 |
| 1,178,898 A | * | 4/1916 | Young | 604/42 |
| 3,288,140 A | | 11/1966 | Maccarthy | 128/248 |
| 3,556,097 A | * | 1/1971 | Wallace | 128/202.23 |
| 3,910,266 A | | 10/1975 | Kawase | 128/66 |
| 4,798,599 A | * | 1/1989 | Thomas | 604/290 |
| 5,037,431 A | | 8/1991 | Summers et al. | 606/131 |
| 5,156,846 A | * | 10/1992 | Petersen et al. | 424/443 |
| 5,242,392 A | * | 9/1993 | Vaughn | 604/80 |
| 5,358,494 A | | 10/1994 | Svedman | 604/313 |
| 5,441,482 A | * | 8/1995 | Clague et al. | 604/35 |
| 5,697,920 A | * | 12/1997 | Gibbons | 604/289 |
| 5,735,833 A | * | 4/1998 | Olson | 604/289 |
| 5,898,211 A | | 4/1999 | Marshall et al. | 257/601 |
| 5,941,859 A | | 8/1999 | Lerman | 604/289 |

(Continued)

FOREIGN PATENT DOCUMENTS

EP    0355186 A    2/1990

(Continued)

*Primary Examiner*—Manuel Mendez
(74) *Attorney, Agent, or Firm*—Winston & Strawn LLP

(57) ABSTRACT

Method and device, including a uniquely operative applicator, and pharmaceutical compositions, for the controlled, non-surgical removal and retrieval of cells from a variety of skin lesions and tissue surfaces are disclosed. A synergistic effect of proteolytic digestion of the intracellular matrix and "stripping" flow is achieved by treating a defined area with a controlled, continuous stream of proteolytic enzyme solution, causing gentle but effective tissue erosion. Isolated cells from the skin lesion and/or tissue surface may be collected from the protease solution stream for histological analysis and/or cell culture, affording a method of "enzymatic biopsy". The protease solution may be supplemented with anesthetics, coagulants, anticoagulants and antibiotics to decrease the discomfort, erythema, bleeding, risk of infection and scarring traditionally associated with surgical treatment of skin lesions. Delivery of precise levels of catalytic activity is ensured by controlled activation of stable, inactivated enzyme stock solutions and powders shortly prior to application.

44 Claims, 11 Drawing Sheets
(2 of 11 Drawing Sheet(s) Filed in Color)

U.S. PATENT DOCUMENTS

| | | | |
|---|---|---|---|
| 5,976,556 A * | 11/1999 | Norton et al. | 424/401 |
| 6,117,433 A | 9/2000 | Edens et al. | 424/400 |
| 6,261,275 B1 | 7/2001 | Hayes | 604/294 |
| 6,264,666 B1 | 7/2001 | Coleman et al. | 606/131 |
| 6,293,929 B1 | 9/2001 | Smith et al. | 604/289 |
| 6,368,595 B2 | 4/2002 | Edens et al. | 424/94.6 |
| 6,398,767 B1 | 6/2002 | Fleischmann | 604/313 |
| 6,406,447 B1 * | 6/2002 | Thrash et al. | 601/160 |
| 6,458,109 B1 | 10/2002 | Henley et al. | 604/304 |
| 6,520,982 B1 | 2/2003 | Boynton et al. | 607/104 |
| 6,942,649 B2 * | 9/2005 | Ignon et al. | 604/289 |

FOREIGN PATENT DOCUMENTS

| | | |
|---|---|---|
| GB | 641061 A | 8/1950 |
| GB | 2378392 A | 2/2003 |

* cited by examiner

80

80

80

CONTROLLED ENZYMATIC REMOVAL AND RETRIEVAL OF CELLS

RELATED APPLICATIONS

This is a continuation-in-part of PCT international patent application No. IL02/00572, filed Jul. 16, 2002, entitled: "Device For And Method Of Controlled Enzymatic Removal And Retrieval Of Tissue", claiming priority from U.S. patent application Ser. No. 09/915,518 filed Jul. 27, 2001, of same title; both specifications of which are incorporated herein by reference.

FIELD AND BACKGROUND OF THE INVENTION

The present invention relates to a method, device, and pharmaceutical compositions, for the controlled removal of cells from the surface of viable tissue by continuous local application of a solution containing a proteolytic enzyme and, more particularly, to a method, device and pharmaceutical composition for non-surgical, enzymatic treatment and biopsy of skin lesions. The method and device each includes a uniquely configured and operative applicator including at least one inlet and at least one outlet, each providing a passageway for streaming of a solution therethrough and over a skin portion defined by a skin-facing opening of a treatment zone of a skin portion of a subject. An opening of at least one of the at least one inlet and the at least one outlet through which the solution streams is height adjustable with respect to the skin-facing opening, such that the applicator physically conforms to a non-smooth skin surface of the subject.

Tissues are composed of individual cells and cell groups, embedded in a proteinaceous extracellular matrix. Collagen fibers are the main component of this ubiquitous network, with other proteins such as fibronectin, laminin, elastin and tenascin, providing a mechanism for cell attachment. Cell surface attachment molecules, such as the CAM proteins, allow cells to adhere to the extracellular matrix and to neighboring cells. Thus, the histological integrity of tissues depends on the interaction of many protein and protein-derived molecules.

Enzymes capable of digesting proteins, or proteases, are commonly employed to disrupt the extracellular matrix of tissues or tissue samples in order to separate cells for establishment of primary cell cultures, for example, as described by Ferkushny, R. I., in "Culture of Animal Cells", p. 108, A R Liss, NY (1983). Proteases used in the isolation of cells for culturing are typically selective in their proteolytic activity or in the method of their application, achieving effective disruption of the matrix and adhesion proteins, yet causing minimal digestion of critical cell components. In the preparation of a primary culture, the tissue is mechanically cut into small (2–3 mm) pieces, these explants washed and gently agitated in an isotonic buttered solution containing a protease, such as trypsin or collagenase, for 30 minutes to several hours at room temperature. This procedure, resulting in suspended, isolated cells, is universal and has been employed for the preparation and propagation of primary cell cultures from a variety of tissues, including skin biopsies, for example, as described by Hybbinette, S., Bostrom, M., and Lindberg, K., in "Enzymatic Disassociation Of Keratinocytes From Human Skin Biopsies For In Vitro Cell Propagation", Experimental Dermatology, 8, 30–38 (1999).

Proteolytic digestion of skin, achieving complete or partial disruption of the tissue, has been applied, typically as an alternative to mechanical means, in a wide variety of industrial, cosmetic, experimental and clinical processes. These include the depilation of animal hides and pelts, for example, as disclosed in DE Patent Application No. 19519436, Nov. 28, 1996, soothing and promotion of healing of skin lesions such as $CO_2$ laser surgery wounds, for example, as described by Gaspar, L. and Bogdanyi, E., in "Clinical Experience With Enzymes In The Treatment Of Skin Lesions Caused By $CO_2$ Laser Surgery", Orv. Hetil. 139, 1475–77 (Hungarian) (1998); and decubitus ulcers, for example, as described by Spoelhof, G. D. and Ide, K., in "Pressure Ulcers In Nursing Home Patients", Am. Fam. Physic. 47, 1207–15 (1993); the debridement of non-viable tissue as in burn eschar, for example, as described by Mekkes, J. R., LePoole, I. C., Das, P. K., Bos, J. D., and Westerhof, H., in "Efficient Debridement Of Necrotic Wounds Using Proteolytic Enzymes Derived From Antarctic Krill", Wound Repair and Regeneration, 6, 50–57 (1998), removal of fibrinous exudate from sensitive regions, such as the eye, for example, as described by Mullaney, P. B., Wheeler, D. T., and al-Nahdi, T., in "Dissolution Of Pseudophakic Fibrinous Exudates With Intraocular Streptokinase", Eye, 10, 362–66 (1996); renewal of aging skin by exfoliation, for example, as disclosed in U.S. Pat. No. 5,976,556 to Norton, et al.; removal of lice nits from hair, for example, as disclosed in U.S. Pat. No. 5,935,572 to Sorenson et al.; and the treatment of infectious lesions of the skin such as acne and leprosy, for example, as disclosed in U.S. Pat. No. 5,958,406 to de Faire et al.

Treatment of Skin Lesions

Treatment of skin lesions such as lentigines, melasmas, keratoses, nevi, keloids, hypertrophic scars, psoriasis, and tattoos requires the removal of diseased or abnormal skin cells. Surgical procedures are generally painful and destructive to the healthy, neighboring tissues, resulting in scarring and abnormal pigmentation of the treated areas, for example, as described by Gambichler, T., Senger, E., Rapp, S., Almouti, D., Altmeyer, P., and Hoffman, K., in "Deep Shave Excision Of Macular Melanocyte Nevi", Dermatol. Surg., July 26 (7), 662–66 (2000), the need for administration of anesthesia, and significant stress trauma to the patient, for example, as described by Augustin, M., Zschocke, I., Godau, N., Buke-Kirschenbaum, A., Peschen, M., Sommer, B., and Sattler, G., in "Skin Surgery Under Local Anesthesia Leads To Stress-induced Alterations Of Psychological, Physical And Immune Functions", Dermat. Surg., November 25 (11), 868–71 (1999). In addition, surgical excision of certain lesions is often complicated by the presence of more than one aberrant cell type, for example, as described by Crawford, J. B., Howes, E. L. Jr., and Char, D. A., in "Conjunctival Combined Nevi", Trans-Am. Ophthamol. Soc., 97, 170–83 (1999), and is inappropriate for sensitive and precarious anatomical regions. These disadvantages of surgical excision of skin lesions have led to the development of non-mechanical methods such as electro-cauterization, electro-ablation, cryosurgery with liquid nitrogen and lasers.

One currently widely used technique employs laser energy directed at the skin lesion to cause ablation of the undesired tissue. Laser surgery, as it is known, is less traumatic to adjoining tissue, due to the cauterization effects of the intense energy, and the ability to carefully focus the laser beam, for example, as described by Raulin, C., Schanermark, M. P., Greve, B., and Werner, S., in "Q-switched Ruby Laser Treatment Of Tattoos And Benign Pigmented Skin Lesions, A Critical Review", Ann. Plast Surg., November 41 (5), 555–65 (1995), producing less pain and scarring than scalpel or razor blade excision techniques. However, there remain the problems of pain and scarring associated with the intense heat required for tissue ablation, poor results with attempts at laser treatment of certain lesions, such as melanocytic and congenital nevi (Raulin, C. et al., same as above) and the importance of removal, rather than ablation of the abnormal tissue for histological analysis to determine the character and extent of the lesion.

Proteolytic Enzymes in Treatment of Skin Lesions

U.S. Pat. No. 4,226,854 to Klein et al.; U.S. Pat. Nos. 5,505,943 and 6,017,531 to Fortney et al.; U.S. Pat. No. 5,106,621 to Rowan et al., and U.S. Pat. No. 5,840,283 to Sorenson et al., teach the use of proteases to achieve removal or permeation of abnormal, devitalized or necrotic skin. Rowan et al. (U.S. Pat. No. 5,106,621) disclose a cysteine protease from pineapple, ananain, in a pharmaceutical preparation for topical application and debridement of burn wounds or ulcerated tissue. Similarly, Fortney et al. (U.S. Pat. Nos. 5,505,943 and 6,017,531) describe the use of the bacterial protease Vibriolysin for debridement of burn eschar and necrotized skin by topical application in a solution or ointment preparation. Sorenson et al. (U.S. Pat. No. 5,840,283) describe the topical use of proteolytic enzymes as permeation facilitators in treatment of diseased nail, claw or hoof tissue. The commercially available ointment Travase™ (U.S. Pat. No, 3,409,719 to Noe et al.) also employs proteolytic activity, found in *Bacillus subtilis* filtrate, for the debridement of burn eschar and decubitus ulcer tissue. In all these, and other similar methods, the proteolytic activity is directed at the removal of non-vitalized tissue and is achieved by individual topical applications with gauze or sponge, with no provision for the control of levels or duration of enzyme activity, or the collection of cells from the treated lesion.

U.S. Pat. No. 5,958,406 to de Faire et al. describes the use of a crustacean multifunctional protease for treatment and prevention of bacterial, fungal and viral infections, blood clots, cell-adhesion-related disease (such as HIV and autoimmune disorders) and skin lesions and infection (such as acne, pruritis and scars). The protease preparation is administered by various methods: topically, in an aqueous or non-aqueous vehicle; parenterally, orally or in suppositories for systemic applications; ocularly, in drops, ointment or aerosol; and in cutaneous or subcutaneous injection, for skin lesions such as scars, acne and boils. However, no mention is made of control of enzyme activity once applied, or of a means of obtaining cells from the treated tissues.

U.S. Pat. No. 5,976,556 to Norton et al. describes the topical application of proteolytic enzymes for exfoliation of skin, and treatment of abnormal conditions and diseases of the skin such as warts, lentigines, melasmas, acne, psoriasis, etc. Control of enzyme activity is effected by the restriction of enzymes to acid proteases, active in their acidic buffer when applied, and inactivated by slow deacidification caused by the normal epidermal pH regulatory mechanism. No ongoing monitoring or control of enzymatic activity is provided, and no mention is made of obtaining cells from the treated tissue.

U.S. Pat. No. 6,146,626 to Markert at al. describes the preparation of a proteolytic enzyme mixture comprising collagenase and elastase from *Clositridium histolyticum*, for application in wound healing and obtaining cells from whole tissue or tissue fragments. Conditions for the topical application of the enzyme to burn wounds, and the isolation of cells from a variety of human and other animal tissue are discussed. However, the procedure described relates to preparation of cells for tissue culture from tissue fragments rather than the therapeutic application of cell removal from live tissue. Furthermore, no provision is made for collection of cells from living tissue in situ.

Autolysis of Proteases

Proteolytic enzymes, being proteins, are in themselves substrates for self-digestion, or autolysis, thus limiting the effectiveness of active, protease based preparations. For example, a commercially available serine protease derived from bacteria of genus *Bacillus* (Subtilisin A., manufactured by Novo Nordisk Bioindustry Japan K.K.) loses its enzymatic activity by about 70%, when it is kept in an aqueous solution at pH 7.0 at 25° C. for 24 hours. Clinical applications employing proteolytic enzymes should provide means of preventing and controlling catalytic inactivation due to autolysis.

Most proteases demonstrate catalytic activity within a defined, and often narrow physico-chemical environment (pH, temperature, ionic strength, solvent polarity, etc.). The specific nature of some proteases may be exploited to prevent autolysis during storage and application of the enzyme, and to allow for the enzymes deactivation after use.

One approach is to store the enzyme in a lyophilized state, to be diluted in an activating buffer of appropriate pH, ionic strength etc. just before or at the time of delivery to the tissue(s) being treated. Enzyme stability is enhanced when dry, but solubility and even dispersal of the enzyme solid in the activating buffer is difficult, resulting in poor control of enzyme activity at point of delivery.

Another method for prolonging and controlling enzyme activity is the separation of enzyme preparations from their activating buffers until use. This separation may be effected physically, storing the enzyme and activating diluent in separate compartments, the enzyme maintained in a stabilized preparation. U.S. Pat. No. 6,228,323 to Asgharian et al. describes a device for storage and delivery of proteolytic enzyme preparations intended for dispensing contact lens cleanser. The enzyme preparations are stabilized by polyols, such as PEG-400, in a concentrated form, and are mixed with the activating diluents, in predetermined ratios, upon dispensing. In U.S. Pat. No. 5,409,546 to Nakagawa et al. a metal chelator is mixed with the stock enzyme preparation, removing the cations necessary for catalytic activity and prolonging shelf life. Introduction of cations in the diluent restores enzymatic activity, also intended for the cleansing of contact lenses.

A similar approach to prevention of autolysis and destabilization of enzyme preparations is described in U.S. Pat. No. 6,117,433 to Edens et al. The effect of polyols on enzyme activity is discussed in detail, as are other enzyme-stabilizing methods such as non-optimal pH, high salt concentrations, etc. The stabilized enzymes, or other biologically active substances, are intended for dispensing with an appropriate amount of activating diluent, for topical application, as in cosmetic preparations, on skin or other external surfaces. No mention is made of removal and retention of cells from treated skin lesions, or of an apparatus for controlled application of a protease solution to a defined and isolated area.

There is thus a widely recognized need for, and it would be highly advantageous to have, a method and device of controlled enzymatic removal and retention of cells from external surfaces of the skin, devoid of the above limitations.

SUMMARY OF THE INVENTION

The present invention is of a method, device, and pharmaceutical compositions, for the continuous topical application of a solution containing a proteolytic enzyme. The method and device each includes a uniquely configured and operative applicator including at least one inlet and at least one outlet, each providing a passageway for streaming of a solution therethrough and over a skin portion defined by a skin-facing opening of a treatment zone of a skin portion of a subject. An opening of at least one of the at least one inlet and the at least one outlet through which the solution streams is height adjustable with respect to the skin-facing opening, such that the applicator physically conforms to a non-smooth skin surface of the subject.

The present invention is generally applicable for the controlled removal and retrieval of cells from the surface of the skin. The present invention is specifically applicable for non-surgical, enzymatic treatment, and biopsies, of skin lesions such as lentigines, melasmas, keratoses, nevi, keloids, hypertrophic scars, psoriasis and tattoos.

Thus, according to one aspect of the present invention, there is provided a method for treating a skin portion of a subject inflicted with a dermatological lesion, which comprises producing a solution containing an effective amount of at least one protease; and directing the solution in the form of a stream into and out of contact with the skin portion such that the solution stream enzymatically and mechanically removes cells from the skin portion.

According to further features in preferred embodiments of the invention described below, the at least one protease is selected from the group consisting of vibriolysin, krill protease, chymotrypsin, trypsin, collagenase, elastase, dipase, proteinase K, *Clostridium* multifunctional protease and *Bacillus subtilis* protease.

According to further features in preferred embodiments of the invention described below, the solution contains a single protease.

According to further features in preferred embodiments of the invention described below, the solution contains a plurality of proteases.

According to further features in preferred embodiments of the invention described below, the solution further contains an effective amount of at least one substance selected from the group consisting of a local anesthetic, a coagulant and an anti-coagulant.

According to further features in preferred embodiments of the invention described below, the solution further contains an effective amount of an antibiotic.

According to further features in preferred embodiments of the invention described below, the at least one protease is activated shortly prior to the streaming of the protease solution, over, and in contact with, the skin portion.

According to further features in preferred embodiments of the invention described below, the at least one protease is activated by a method selected from the group consisting of: keeping the at least one protease at a first temperature in which the at least one protease is substantially catalytically inactive and heating and/or cooling the at least one protease to a second temperature in which the at least one protease is catalytically active, providing the at least one protease in a powder form and mixing the powder with a solution in which the at least one protease is catalytically active, and providing the at least one protease in a first solution in which the at least one protease in substantially catalytically inactive and mixing the first solution with a second solution so as to achieve a mixed solution in which the at least one protease is catalytically active.

According to further features in preferred embodiments of the invention described below, tie mixed solution differs from the first solution by at least one parameter selected from the group consisting of pH, ion concentration, free metal concentration, hydrophilicity and hydrophobicity.

According to further features in preferred embodiments of the invention described below, the dermatological lesion is selected from the group consisting of warts, lentigines, melasmas, acne, keratoses, nevi, keloids, hypertrophic scars, psoriasis and tattoos.

According to further features in preferred embodiments of the invention described below, the method further includes the step of: (g) collecting the streaming protease solution and the removed cells exiting the outlet port.

According to further features in preferred embodiments of the invention described below, the collecting the removed cells is effected via filtration.

According to further features in preferred embodiments of the invention described below, the collecting the removed cells is effected via continuous flow centrifugation.

According to another aspect of the present invention, there is provided a method of removing cells from the surface of a viable tissue of a subject, comprising the steps of: (a) providing a first reservoir containing a solution containing an effective amount of at least one protease; (b) providing an applicator in fluid communication with the first reservoir, for restricting streaming of the protease solution, over, and in contact with, the surface of the viable tissue; (c) receiving the protease solution from the first reservoir via an inlet port of the applicator; (d) directing the streaming of the protease solution from the inlet port to a treatment zone of the surface of the viable tissue, via a first tube structure of the applicator operatively connected to the inlet port, such that the streaming protease solution enzymatically and mechanically causes the removal of cells from the surface of the viable tissue; (e) adjustably directing the streaming protease solution and the removed cells away from the treatment zone via a second tube structure positioned within the first tube structure, wherein a screw mechanism operatively connected to the second tube structure allows adjustment of height of opening of the second tube structure with respect to a skin-facing opening of the treatment zone; and (f) removing the streaming protease solution and the removed cells from the second tube structure, via an outlet port operatively connected to the second tube structure, thereby removing the cells from the surface of the viable tissue of the subject.

According to another aspect of the present invention, there is provided an applicator for applying a solution containing an effective amount of at least one protease to a skin portion of a subject for treatment thereof, the applicator comprising: a body member having an open end defining an annular surface to be brought into contact with the skin portion to thereby define a confined space therewith; at least one inlet into the body member communicating with the confined space via a first passageway for applying the solution to the skin portion within the confined space; at least one outlet from the body member communicating with the confined space via a second passageway through the body member for outletting therefrom the solution after applied to the surface of the object within the confined space; and a source of the protease solution to be inletted via the inlet and to be streamed into and out of contact with the skin portion of the subject for enzymatically and mechanically removing cells therefrom. In particular, this applicator is used for removing cells from a skin portion of a subject, and comprises: (a) an inlet port operatively connectable to a first reservoir containing a solution containing an effective amount of at least one protease, for being in fluid communication with the first reservoir, for receiving the protease solution from the first reservoir; (b) a first tube structure operatively connected to the inlet port for directing streaming of the protease solution from the inlet port to a treatment zone of the skin portion, such that the streaming protease solution streams over, and in contact with, the skin portion, for enzymatically and mechanically causing the removal of cells from the skin portion; (c) a second tube structure positioned within the first tube structure for adjustably directing the streaming protease solution and the removed cells away from the treatment zone, wherein a screw mechanism operatively connected to the second tube structure allows adjustment of height of opening of the second tube structure with respect to a skin-facing opening of the treatment zone; and (d) an outlet port operatively connected to the second tube structure for removing the streaming protease solution and the removed cells from the second tube structure, thereby removing the cells from the skin portion of the subject.

According to further features in the described preferred embodiment, the body member is a housing having an open end mounting a head; and the flexible plastic material is in the form of a flexible skirt of plastic material carried by the head and formed with an annular rim to contact the surface of the object to be treated; the head being threadedly mounted on the housing to permit axial adjustment of the distance between the annular rim of the skirt, and at least one of the passageways, to accommodate irregularities in the surface of the object to be treated.

According to further features in preferred embodiments of the invention described below, the applicator is used for treating the skin of a subject infected with a dermatological lesion. In this application of the invention, the applicator further includes a reservoir holding a supply of a protease solution to be inletted via the inlet port and to be streamed into and out of contact with the skin of the subject for enzymatically and mechanically removing cells from the skin. A pump may be operatively connected between the first reservoir and the inlet port for providing this pressure and effecting the streaming of the protease solution from the first reservoir to the inlet port. Alternatively, the pressure and streaming may be effected by gravitation.

According to further features in preferred embodiments of the invention described below, the device further includes a thermoregulator for heating and/or cooling the protease solution.

According to further features in preferred embodiments of the invention described below, the device further includes a mixer for mixing the protease solution.

According to further features in preferred embodiments of the invention described below, the device further includes a filter for filtering the protease solution.

According to further features in preferred embodiments of the invention described below, the device further includes: a second reservoir containing the at least one protease in a first solution in which the at least one protease is substantially catalytically inactive; and a third reservoir containing a protease activating solution, the activating solution activates catalytic activity of the at least one protease upon mixing with the first solution; the second reservoir and the first reservoir are in fluid communication with the third reservoir.

According to further features in preferred embodiments of the invention described below, the device further includes a second reservoir for containing a protease activating solution, the activating solution activates catalytic activity of the at least one protease upon mixing therewith.

According to further features in preferred embodiments of the invention described below, the device further includes a cell collector in fluid communication with the applicator, for receiving the streaming protease solution and the removed cells from the outlet port.

According to further features in preferred embodiments of the invention described below, the cell collector includes a filter for collecting the removed cells from the skin portion of the subject.

According to further features in preferred embodiments of the invention described below, the cell collector includes a continuous flow centrifuge for collecting the removed cells from the skin portion of the subject.

According to further features in preferred embodiments of the invention described below, the device further includes an engaging mechanism for engaging the applicator to the skin portion of the subject.

According to further features in preferred embodiments of the invention described below, the device further includes a receptacle for receiving the first reservoir.

According to another aspect of the present invention, there is provided a device for removing cells from a surface portion of a subject, comprising: (a) a first reservoir containing a first solution containing an effective amount of at least one protease in a substantially catalytically inactive form; (b) a first receptacle for receiving the first reservoir; (c) a second reservoir containing a protease activating solution, the activating solution activates catalytic activity of the at least one protease upon mixing with the first solution; (d) a second receptacle for receiving the second reservoir; (e) a mixing chamber in fluid communication with the first and second reservoirs when received by the first and second receptacles, the mixing chamber is for mixing the first solution and the activating solution such that the at least one protease becomes catalytically active in solution; (f) an applicator in fluid communication with the mixing chamber, for restricting streaming of the active protease solution, over, and in contact with, the skin portion, the applicator includes: (i) an inlet port for receiving the active protease solution from the mixing chamber; (ii) a first tube structure operatively connected to the inlet port for directing the streaming of the active protease solution from the inlet port to a treatment zone of the skin portion, such that the streaming active protease solution enzymatically and mechanically causes the removal of cells from the skin portion; (iii) a second tube structure positioned within the first tube structure for adjustably directing the streaming active protease solution and the removed cells away from the treatment zone, wherein a screw mechanism operatively connected to the second tube structure allows adjustment of height of opening of the second tube structure with respect to a skin-facing opening of the treatment zone; and (iv) an outlet port operatively connected to the second tube structure for removing the streaming active protease solution and the removed cells from the second tube structure, thereby removing the cells from the skin portion of the subject.

According to another aspect of the present invention, there is provided a device for removing cells from a skin portion of a subject, comprising: (a) a first reservoir containing an effective amount of at least one protease in a non-aqueous catalytically inactive form; (b) a first receptacle for receiving the first reservoir; (c) a second reservoir containing a protease activating solution, the activating solution activates catalytic activity of the at least one protease upon mixing with the at least one protease; (d) a second receptacle for receiving the second reservoir; (e) a mixing mechanism in fluid communication with the first and second reservoirs when received by the first and second receptacles, the mixing mechanism is for mixing the at least one protease and the activating solution such that the at least one protease becomes catalytically active in solution; (f) an applicator in fluid communication with the mixing mechanism, for restricting streaming of the active protease solution, over, and in contact with, the skin portion, the applicator includes: (i) an inlet port for receiving the active protease solution from the mixing mechanism; (ii) a first tube structure operatively connected to the inlet port for directing the streaming of the active protease solution from the inlet port to a treatment zone of the skin portion, such that the streaming active protease solution enzymatically and mechanically causes the removal of cells from the skin portion; (iii) a second tube structure positioned within the first tube structure for adjustably directing the streaming active protease solution and the removed cells away from the treatment zone, wherein a screw mechanism operatively connected to the second tube structure allows adjustment of height of opening of the second tube structure with respect to a skin-facing opening of the treatment zone; and (iv) an outlet port operatively connected to the second tube structure for removing the streaming active protease solution and the removed cells from the second tube structure, thereby removing the cells from the skin portion of the subject.

According to another aspect of the present invention, there is provided an applicator for removing cells from a skin portion of a subject, comprising: (a) an inlet port operatively connectable to a first reservoir containing a solution containing an effective amount of at least one protease, for being in fluid communication with the first reservoir, for receiving the protease solution from the first reservoir; (b) a first tube structure operatively connected to the inlet port for directing streaming of the protease solution from the inlet port to a treatment zone of the skin portion, such that the streaming protease solution streams over, and in contact with, the skin portion, for enzymatically and mechanically causing the removal of cells from the skin portion; (c) a second tube structure positioned within the first tube structure for adjustably directing the streaming protease solution and the removed cells away from the treatment zone, wherein a screw mechanism operatively connected to the second tube structure allows adjustment of height of opening of the second tube structure with respect to a skin-facing opening of the treatment zone; and (d) an outlet port operatively connected to the second tube structure for removing the streaming protease solution and the removed cells from the second tube structure, thereby removing the cells from the skin portion of the subject.

According to further features in preferred embodiments of the invention described below, for the applicator, a pump is operatively connected between the first reservoir and the inlet port for effecting the streaming of the protease solution.

According to further features in preferred embodiments of the invention described below, for the applicator, the streaming of the protease solution from the first reservoir to the inlet port is effected by gravitation.

According to further features in preferred embodiments of the invention described below, for the applicator, a thermoregulator is operatively connected between the first reservoir and the inlet port for heating and/or cooling the protease solution.

According to further features in preferred embodiments of the invention described below, for the applicator, a mixer is operatively connected between the first reservoir and the inlet port for mixing the protease solution.

According to further features in preferred embodiments of the invention described below, for the applicator, a filter is operatively connected between the first reservoir and the inlet port for filtering the protease solution.

According to further features in preferred embodiments of the invention described below, for the applicator, operatively connected between the first reservoir and the inlet port are: a second reservoir containing the at least one protease in a first solution in which the at least one protease is substantially catalytically inactive; and a third reservoir containing a protease activating solution, the activating solution activates catalytic activity of the at least one protease upon mixing with the first solution; the second reservoir and the first reservoir are in fluid communication with the third reservoir.

According to further features in preferred embodiments of the invention described below, for the applicator, operatively connected between the first reservoir and the inlet port is a second reservoir for containing a protease activating solution, the activating solution activates catalytic activity of the at least one protease upon mixing therewith.

According to further features in preferred embodiments of the invention described below, for the applicator, a cell collector is operatively connected to the outlet port, for receiving the streaming protease solution and the removed cells from the outlet port.

According to further features in preferred embodiments of the invention described below, for the applicator, the cell collector comprises a filter for collecting the removed cells from the skin portion of the subject.

According to further features in preferred embodiments of the invention described below, for the applicator, the cell collector comprises a continuous flow centrifuge for collecting the removed cells from the skin portion of the subject.

According to further features in preferred embodiments of the invention described below, for the applicator, an engaging mechanism is operatively connected to the applicator, for engaging the applicator to the skin portion of the subject.

According to further features in preferred embodiments of the invention described below, for the applicator, a receptacle is operatively connected to the first reservoir, for receiving the first reservoir.

According to another aspect of the present invention, there is provided an applicator for removing cells from the surface of a viable tissue of a subject, comprising: (a) an inlet port operatively connectable to a first reservoir containing a solution containing an effective amount of at least one protease, for being in fluid communication with the first reservoir, for receiving the protease solution from the first reservoir; (b) a first tube structure operatively connected to the inlet port for directing streaming of the protease solution from the inlet port to a treatment zone of the surface of the viable tissue, such that the streaming protease solution streams over, and in contact with, the surface of the viable tissue, for enzymatically and mechanically causing the removal of cells from the surface of the viable tissue; (c) a second tube structure positioned within the first tube structure for adjustable directing the streaming protease solution and the removed cells away from the treatment zone, wherein a screw mechanism operatively connected to the second tube structure allows adjustment of height of opening of the second tube structure with respect to a skin-facing opening of the treatment zone; and (d) an outlet port operatively connected to the second tube structure for removing the streaming protease solution and the removed cells from the second tube structure, thereby removing the cells from the surface of the viable tissue of the subject.

According to another aspect of the present invention, there is provided an applicator for streaming a solution over, and in contact with, a skin portion of a subject, the applicator comprising a housing having a skin-facing opening, at least one inlet and at least one outlet, the at least one inlet and the at least one outlet each providing a passageway for streaming of the solution therethrough and over the skin portion defined by the skin-facing opening, wherein an opening of at least one of the at least one inlet and the at least one outlet through which the solution streams is height adjustable with respect to the skin-facing opening, such that the applicator physically conforms to a non-smooth skin surface of the subject.

According to further features in preferred embodiments of the invention described below, the applicator further includes a screw mechanism for adjusting the height of a the opening with respect to the skin-facing opening.

According to further features in preferred embodiments of the invention described below, for the applicator, each the passageway is configured as a tube structure.

According to further features in preferred embodiments of the invention described below, for the applicator, an outlet is positioned within a the inlet.

According to further features in preferred embodiments of the invention described below, for the applicator, the inlet is for adjustably directing streaming of a protease solution to a treatment zone of a surface of a viable tissue of the skin portion of the subject, such that the streaming protease solution streams over, and is in contact with, the surface of the viable tissue, for enzymatically and mechanically causing removal of cells from the surface of the viable tissue of the skin portion of the subject.

According to further features in preferred embodiments of the invention described below, for the applicator, the outlet is for adjustably removing a streaming protease solution and removed cells from a surface of a viable tissue of the skin portion of the subject.

According to further features in preferred embodiments of the invention described below, for the applicator, each opening of the at least one inlet and of the at least one outlet through which the solution streams is height adjustable with respect to the skin-facing opening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

Figure 1:
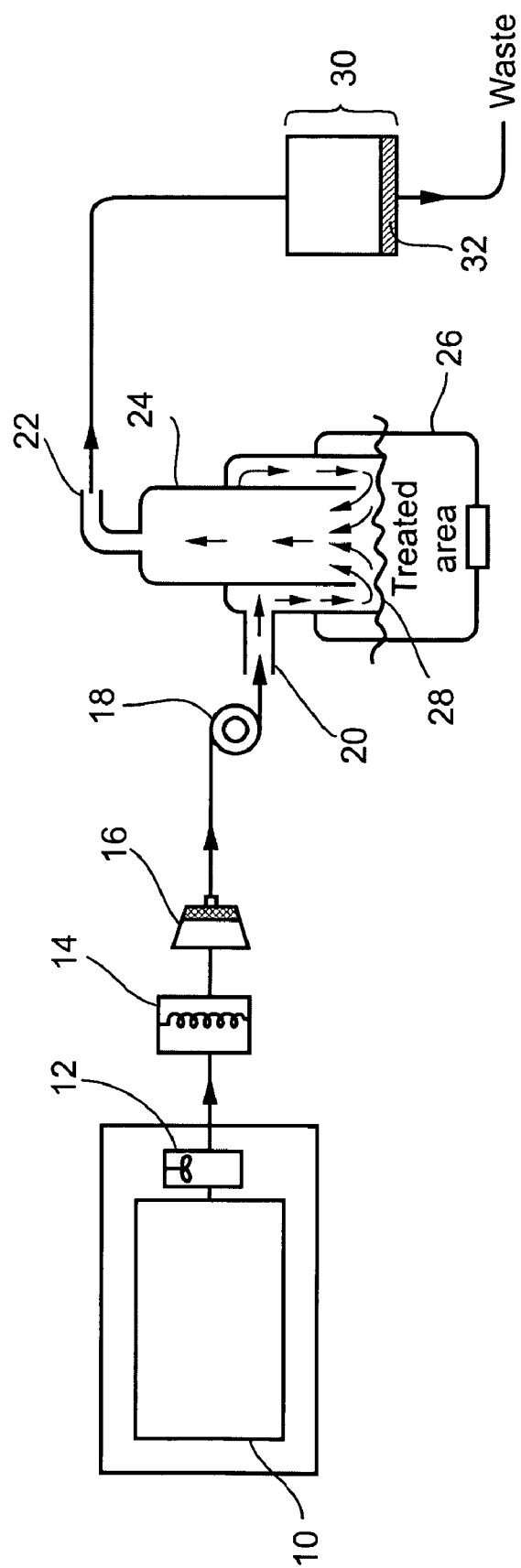
FIG. 1 is a cross-sectional view of a device in accordance with one embodiment of the present invention.

The present invention is of a method, device, and pharmaceutical compositions, for the continuous topical application of a solution containing a proteolytic enzyme. The method and device each includes a uniquely configured and operative applicator including at least one inlet and at least one outlet, each providing a passageway for streaming of a solution therethrough and over a skin portion defined by a skin-facing opening of a treatment zone of a skin portion of a subject. An opening of at least one of the at least one inlet and the at least one outlet through which the solution streams is height adjustable with respect to the skin-facing opening, such that the applicator physically conforms to a non-smooth skin surface of the subject.

The present invention is generally applicable for the controlled removal and retrieval of cells from the surface of the skin. The present invention is specifically applicable for non-surgical, enzymatic treatment, and biopsies, of skin lesions such as lentigines, melasmas, keratoses, nevi, keloids, hypertrophic scars, psoriasis and tattoos.

Structure, function, and principles of operation, of the method, device, and pharmaceutical compositions, for the controlled removal and retrieval of cells from the surface of the skin, according to the present invention, is better understood with reference to the drawings and accompanying descriptions.

It is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As shown in FIGS. 1–9, according to the present invention there is provided a device for streaming and collecting a solution containing an effective amount of protease over, and in contact with, a skin portion, herein referred to below as device 80. FIG. 10 is a cross sectional view of an exemplary specific preferred embodiment of the applicator 24 included in device 80 of the present invention, which is applicable for practicing the present invention on skin.

One preferred embodiment of device 80 is illustrated in FIG. 1. Device 80 according to this embodiment, comprises a first reservoir 10 for holding a solution containing an effective amount of at least one protease. First reservoir 10 may be constructed of durable, inert, non-porous material for repetitive uses, such as glass, metal or plastic. First reservoir 10 may be sanitized between uses by methods well known to one skilled in the art, including by moist or dry heat, or the use of antiseptics, gas or radiation. In another preferred embodiment, first reservoir 10 is constructed of non-durable, disposable material such as metal foil, plastic or foil-laminated or impregnated cardboard or paper, for single use, sterilized and sealed for storage. Dimensions of first reservoir 10 may be adequate for containing a volume of protease solution sufficient to complete a single enzymatic surgery procedure, or smaller, necessitating replenishment during the procedure. First reservoir 10 is typically about one liter in volume, but may vary from 100 milliliters to several liters.

In a preferred embodiment, a mixer 12 for mixing the protease solution is in fluid communication with first reservoir 10, for preventing inconsistent distribution of the protease solution ingredients. Mixer 12 may be external to first reservoir 10, or indwelling. Mixing may be accomplished by rotary motion, as of an impeller or vane within a chamber, or by a rocking or turning oscillatory motion, as of a rocking or rotating platform.

In another preferred embodiment, first reservoir 10 is in fluid communication with a thermoregulator 14, for heating and/or cooling the protease solution to optimal temperature for activation of catalytic activity. Thermoregulator 14 may be a radiantly or convection-heated open chamber, receiving the stream of protease solution, or, preferably a heated and/or cooled fluid bath or solid block receiving a fluid communication element, such as glass or plastic tubing, eliminating direct fluid contact of the stream of protease with thermoregulator 14 and reducing risk of contamination of the protease solution with desired contaminants.

As used herein the phrase "in fluid communication" refers mainly to the capability of selective or non-selective transfer of fluid and/or semi-fluid substances between the specified elements. Such transfer may be accomplished by, for example, channels, tubes, membranes, conduits, pores and/or capillaries.

In yet a further embodiment of the present invention, first reservoir 10 is in fluid communication with a filter 16 which serves for sterilization of the protease solution prior to its application. Filter 16 is preferably a sealed (except for inlet and outlet ports), sterilized housing containing a filtering member excluding particles greater than, for example, 0.25 microns, eliminating common bacterial contamination. One such commercially available filter is distributed under the name Complete Sterifil System (Sigma Chemical Company, Inc.). In a further embodiment of the present invention, first reservoir 10 is in fluid communication with a pump 18 which serves for streaming the protease solution from first reservoir 10 to an applicator 24 (illustratively described in detail hereinbelow) under positive pressure. Thus, the protease solution is delivered to the site of treatment with sufficient force to effect a mechanical, "stripping" action in addition to the enzymatic digestion of matrix proteins. The novel combination of a directional, mechanical force and enzymatic disruption of the lesion tissue provided by the present invention enables the removal of cells and tissue from the treated surfaces.

Pump 18 may be an air pump, a piston-driven fluid pump, syringe pump or an impeller. In one embodiment of the present invention, pump 18 is preferably a variable-speed peristaltic pump, operating through pressure on a flexible fluid communication element eliminating direct fluid contact with the protease solution and subsequent risk of contamination. The variable speed feature further affords control of the intensity of the stream of protease solution applied to the dermatological lesion. One such commercially available peristaltic pump is distributed under the name Masterflex Economy (Aldrich Chemical Company, Inc.). In an alternative embodiment of the present invention, streaming the protease solution is effected by gravitation assisted by elevating first reservoir 10 substantially above other elements in fluid communication therewith.

In general, applicator 24 is for streaming a solution over, and in contact with, a skin portion. Applicator 24 includes a housing having a skin-facing opening, at least one inlet and at least one outlet. The at least one inlet and the at least one outlet each providing a passageway for streaming of the solution therethrough and over the skin portion defined by the skin-facing opening, wherein an opening of at least one of the at least one inlet and the at least one outlet through which the solution streams is height adjustable, such that applicator 24 physically conforms to a non-smooth skin surface.

Applicator 24 is in fluid communication with first reservoir 10, and is designed and constructed to restrict the stream of the protease solution over, and in contact with the skin portion undergoing treatment. Applicator 24 comprises two ports, inlet port 20 serves for receiving the protease solution from first reservoir 10, and outlet port 22 which serves for removing the protease solution and cells from the treated dermatological lesion. Applicator 24 further comprises a recessed skin-facing surface 28, enclosed by the downward projecting outer rim of applicator 24, creating a confined, local area of treatment, preventing exposure of neighboring tissue to proteolytic activity.

Figure 8:
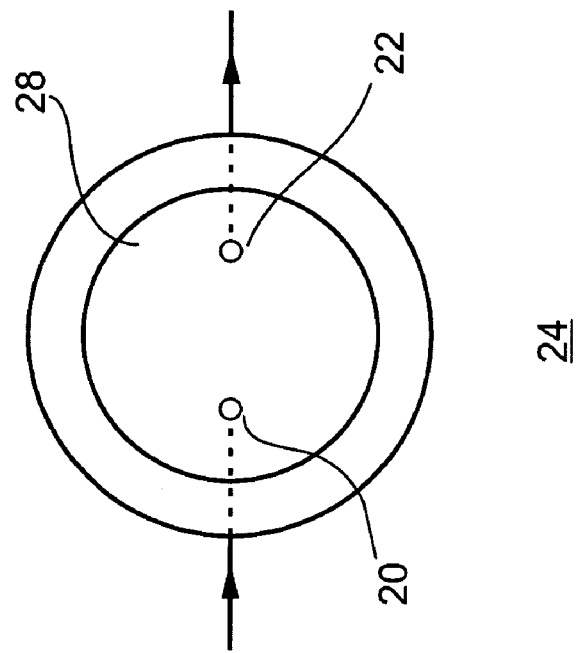
FIG. 8 is an enlarged, cross-sectional view of the protease solution applicator and engaging mechanism according to the present invention.
Figure 9:
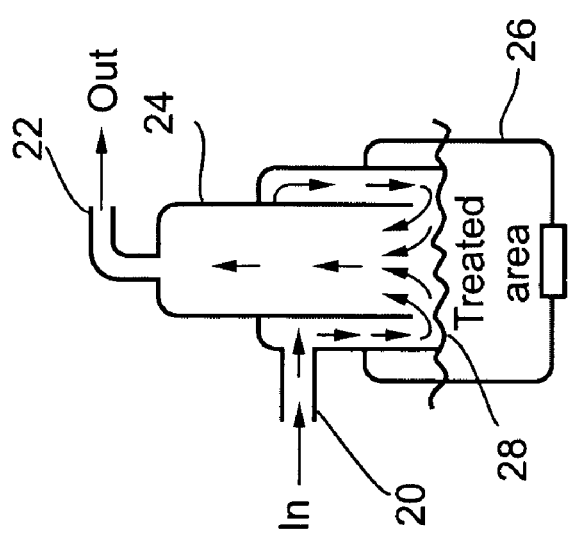
FIG. 9 is an enlarged, bottom (skin-facing surface) view of the protease solution applicator, including the protease solution inlet and outlet ports, according to the present invention.
Figure 10:
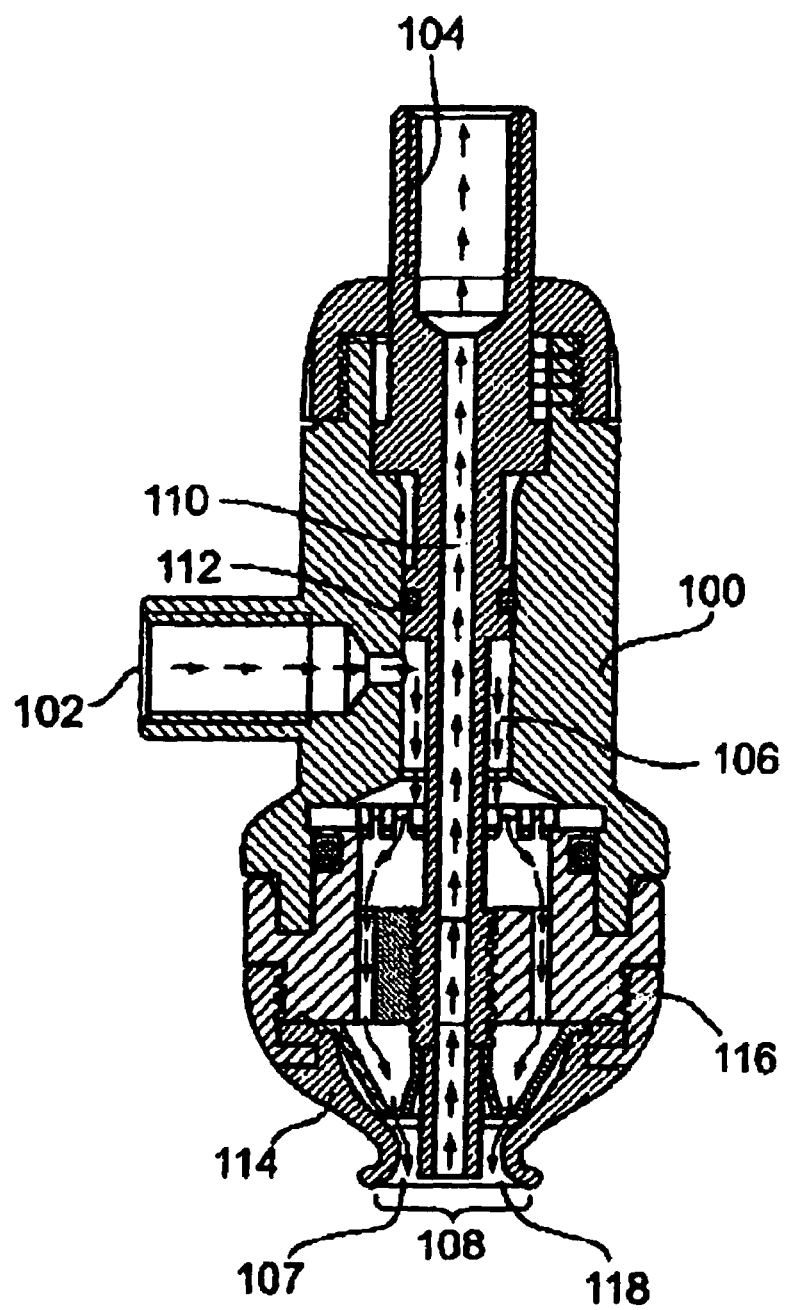
FIG. 10 is a cross sectional view of an exemplary specific preferred embodiment of the applicator included in the device of the present invention, which is applicable for practicing the present invention on skin.

One presently preferred embodiment of applicator 24 is illustrated in FIGS. 8 and 9, and an exemplary specific preferred embodiment of applicator 24 is illustrated in FIG. 10. Inlet port 20 and outlet port 22 provide directional fluid motion for the stream of protease solution, enabling a mechanical "stripping" effect enhancing the enzymatic disruption of the intracellular matrix and removal of cells from the treated lesion surface. Applicator 24 may be engaged with the skin surface by skin-ward pressure applied by attendant operators or treated subject, weight, adhesive connection to adjacent skin surfaces or other means, suitable for the body part bearing the lesion to be treated. In one preferred embodiment applicator 24 comprises an engaging mechanism 26, which comprises two or more flexible elements adjustably connected to allow encirclement of a cylindrical body part (such as a limb or torso) and application of skin-ward pressure through tension, such as a strap and buckle or toothed belt fastener.

Applicator 24 may be constructed of durable, non-porous material including, but not limited to, glass, metal, plastic or rubber, and may be reuseable or preferably disposable. Applicator 24 is preferably capable of sterilization by gas, chemicals, moist or dry heat, or radiation, and is supplied sealed and sterilized for use. In one alternative embodiment, applicator 24 is a "push-pull" cannula typically employed in tissue perfusion techniques, for example, as described by Arancibia, S., in "Push-pull Perfusion Technic In Neuroendocrinology", Ann Endocrinol (Paris) 48:5, 410–18 (1987), which comprises an inflow tube recessed within a wider, outflow tube, creating localized flow of protease solution confined to the outer diameter of the wider, outflow tube.

According to the present invention device 80 preferably further comprises a cell collector 30 which is in fluid communication with first reservoir 10 and applicator 24, and which serves for receiving the protease solution and cells removed from the treated lesion surface, and for providing outflow of waste fluid or fluid to be recycled through device 80. Collected cells are thus made available for histological examination and/or cell culture procedures. In one preferred embodiment cell collector 30 comprises a filter 32 for collection and separation of cells removed from the dermatological lesion. Collector 30 and filter 32 are preferably supplied as a sterile, disposable modular element, such as the Complete Sterifil System (Sigma, Israel). In a further embodiment of the present invention, which is specifically illustrated in FIG. 2, separation of the fluid and cellular fractions in cell collector 30 is effected by continuous flow centrifuge 40. Continuous flow centrifugation provides increased liquid handling capacity, removing the protease solution outflow quickly upon arrival from applicator 24 and concentrating lesion cells for examination and/or culturing.

It will be appreciated, in the context of the present invention that lesion cells collected by cell collector 30 are exposed to protease activity during separation from the fluid component of the protease stream arriving at cell collector 30. Preservation of the cells' morphological and metabolic integrity, and therefore diagnostic value, may depend, in part, on limitation of their prolonged contact with protease. Thus, in one preferred embodiment of the present invention, cell collector 30 is constructed to allow removal and/or sampling of collected cells in mid-process. This may be effected by periodic cessation of streaming of protease solution through applicator 24, removal of the filter element of filter 32, and replacement with a fresh filter element. Alternatively, the entire cell collector 30 may be replaced during operation with a fresh cell collector unit. Where continuous flow centrifuge 40 is the means of cell collection, centrifuge operation may be periodically halted to allow removal of the collected cells from the centrifuge rotor. More preferably, the centrifuge will provide a continuous outflow of concentrated cells for examination and/or cell culture.

It will be noted that the fluid outflow from cell collector 30 contains largely still active protease solution, devoid of the cellular and tissue debris fractions removed by filter 32 and/or centrifuge 40 which may be recycled for reuse. Thus, in one preferred embodiment the fluid outflow of cell collector 30 is reintroduced to the stream of at least one protease solution "upstream" of applicator 24 and pump 18. Fluid communication between the cell collector outflow and the stream of protease solution may be effected by a one-way valve connection, ensuring uni-directional streaming of fluid towards applicator 24. Thus, significant economy of operation is achieved by reuse of the cell collector 30 outflow, effectively reducing the volume of protease solution required per treatment.

Additional embodiments of enzymatic surgery device 80 are depicted in FIGS. 3–7; in each case thermoregulator 14, filter 16, pump 18, applicator 24 and cell collector 30 are substantially as described in the preceeding sections.

Figure 3:
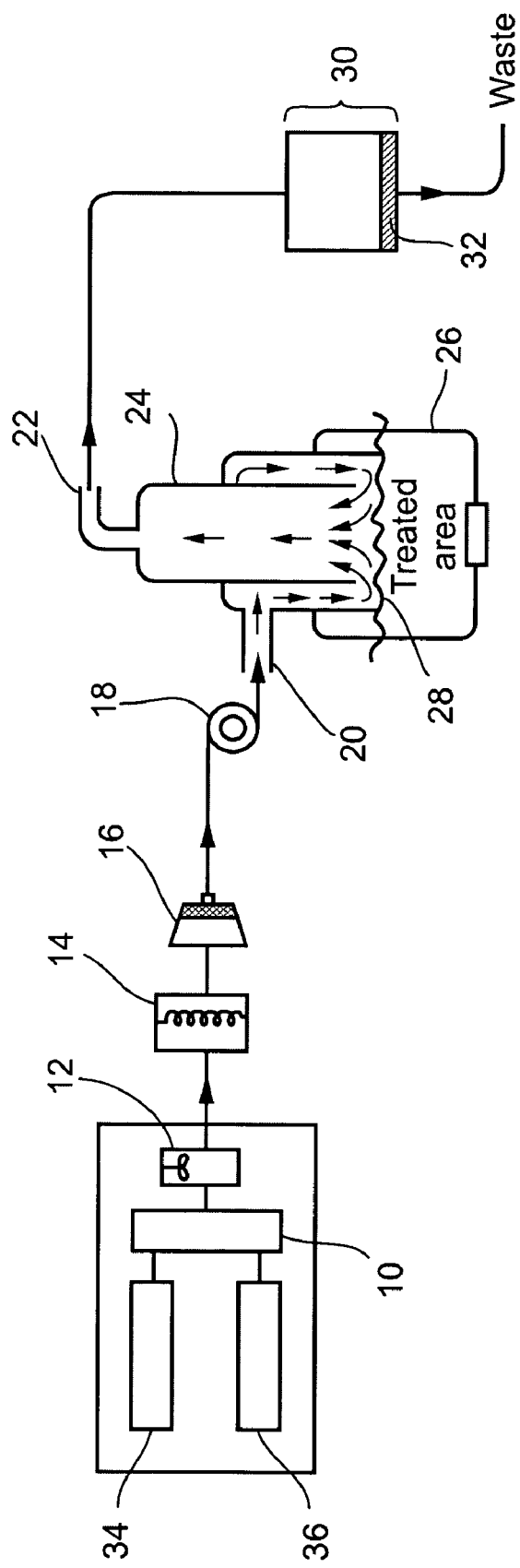
FIG. 3 is a cross sectional view of a device in accordance with yet another embodiment of the present invention.

In one embodiment, illustrated in FIG. 3, device 80 comprises, in addition to first reservoir 10, a second reservoir 34 and a third reservoir 36, which serve for containing a first, substantially inactive protease solution and a second, protease activating solution, respectively. Thus, the protease solution may be prepared and stored in a stabilized, inactive form prior to use, acquiring substantial catalytic activity only after admixing with the activating solution in first reservoir 10.

Figure 4:
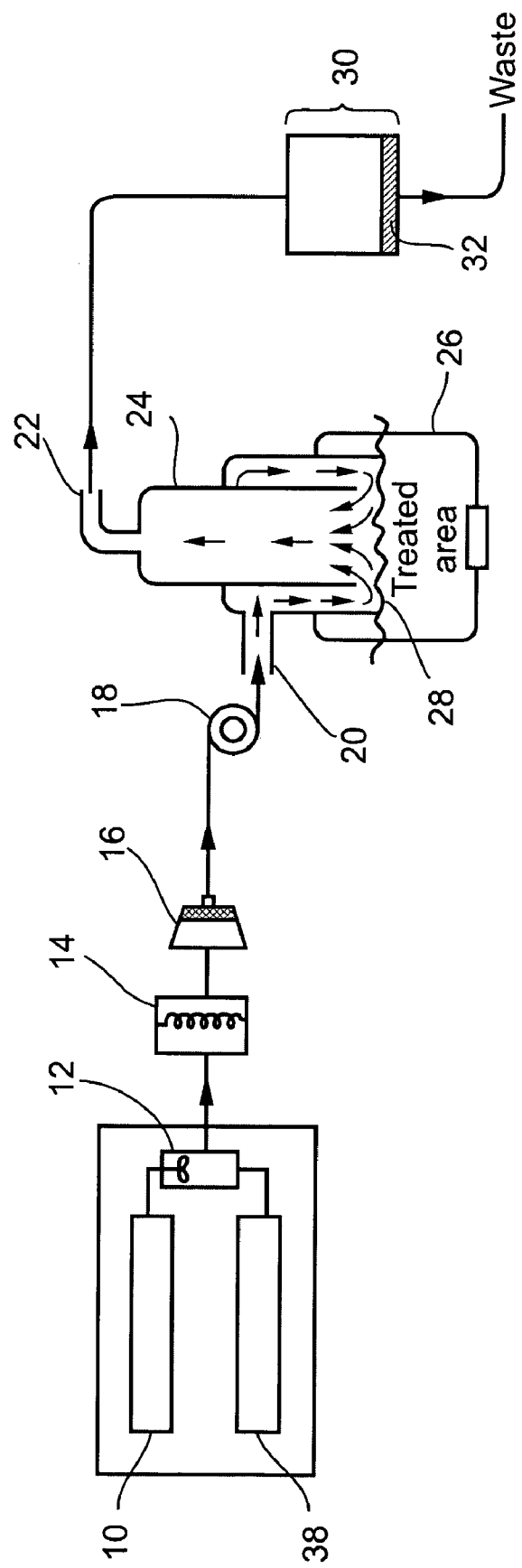
FIG. 4 is a cross sectional view of a device in accordance with still another embodiment of the present invention.

In yet a further embodiment, illustrated in FIG. 4, enzymatic surgery device 80 comprises first reservoir 10 and second reservoir 38, for containing a first, substantially inactive protease and a second, activating solution, respectively. Thus, powdered, lyophilized, and/or other, non-aqueous, stabilized protease preparation(s) placed in first reservoir 10 may be stored until use, minimizing autolysis and loss of catalytic activity. First 10 and second 38 reservoirs are in fluid communication, providing a catalytically active protease solution upon nixing of their contents by mixer 12

Figure 5:
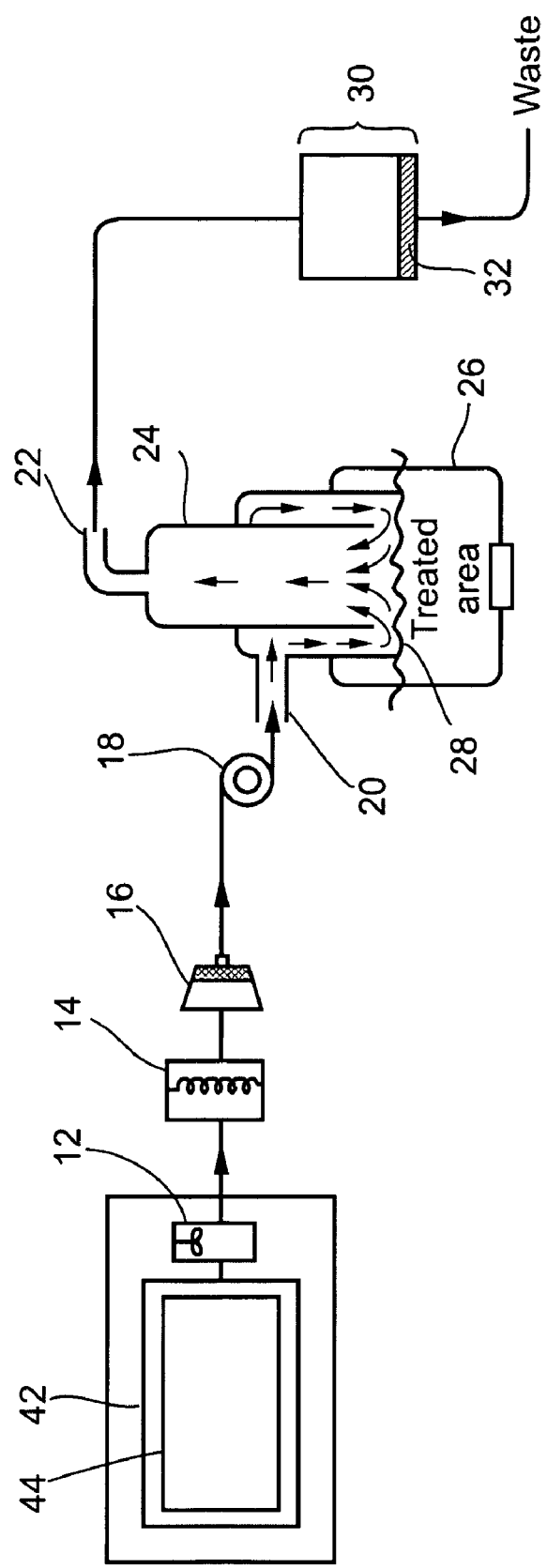
FIG. 5 is a cross sectional view of a device in accordance with an additional embodiment of the present invention.
Figure 6:
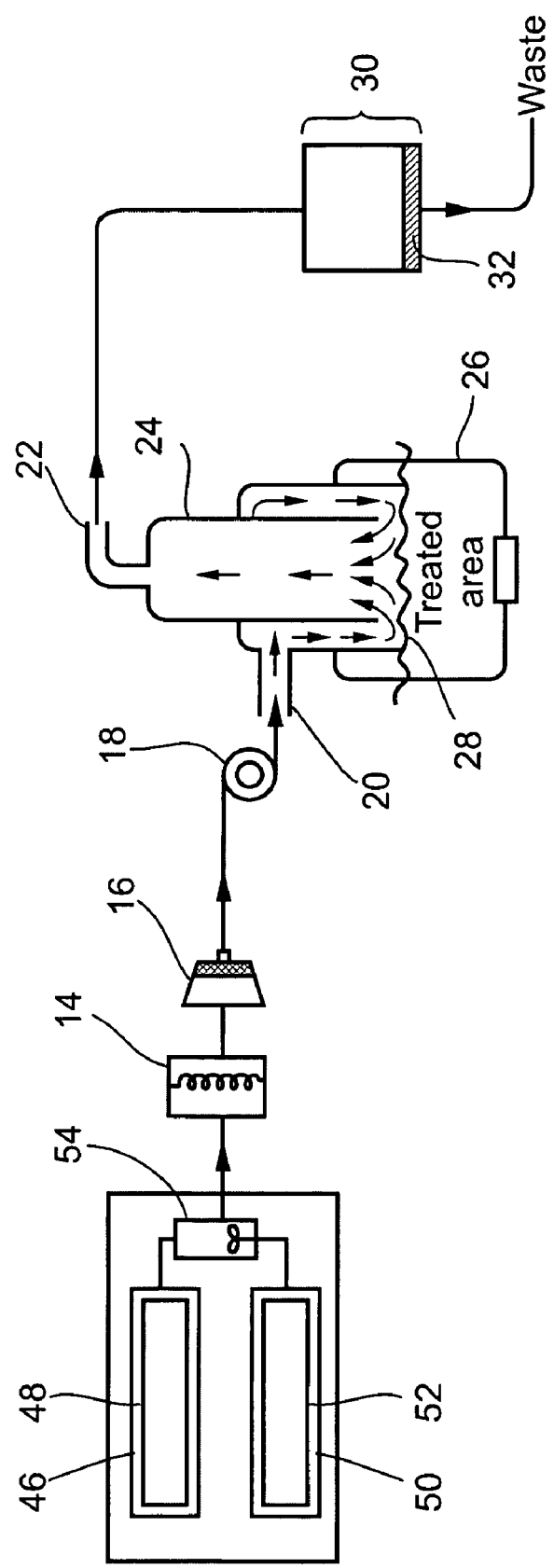
FIG. 6 is a cross sectional view of a device in accordance with yet an additional embodiment of the present invention.
Figure 7:
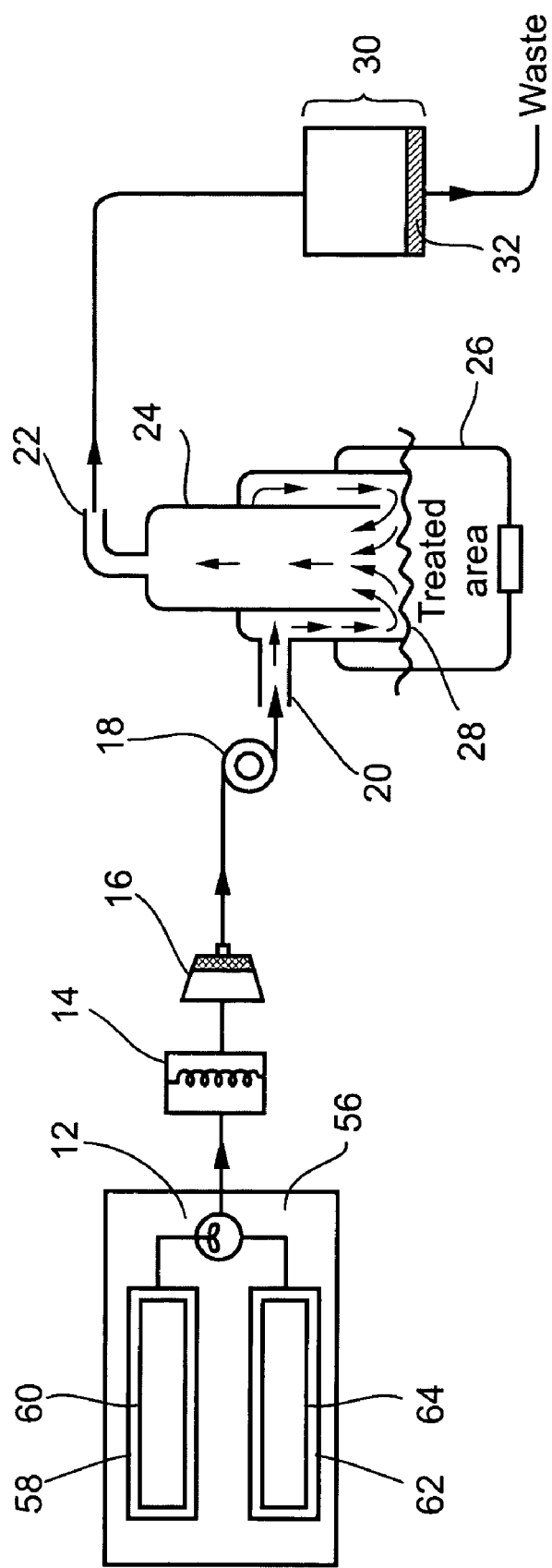
FIG. 7 is a cross sectional view of a device in accordance with still an additional embodiment of the present invention.

FIGS. 5–7 depict enzymatic surgery device 80 designed to receive prepared reservoirs or ampoules of protease, protease solution and/or protease activating solution. In one embodiment, illustrated in FIG. 5, a receptacle 42 is designed to receive modular reservoir or ampoule 44, containing catalytically active protease solution, effecting fluid communication with applicator 24, cell collector 30 and additional "downstream" elements of device 80. Thus, device 80 may be operated with standardized, pre-prepared, stored protease solution(s), increasing simplicity of use and accuracy of protease activity delivered, and decreasing risk of contamination of treated skin surfaces.

As used herein in the specification and in the claims section below, the terms "reservoir" and "ampoule" interchangeably refer to a separate, enclosed container capable of establishing fluid communication with other containers, receptacles or devices. Such reservoirs or ampoules typically contain fluids or fluid-like substances, and may be designed to be accurately engaged by a complementary receptacle or housing. Sealed reservoirs or ampoules provide convenient, standardized means of preparation and storage of active solutions and reagents for the operation of, for example, enzymatic surgery device 80.

In yet another embodiment, illustrated in FIG. 6, first receptacle 46 receives first modular reservoir or ampoule 48, which contains inactivated, stabilized protease solution, while second receptacle 50 receives second modular reservoir or ampoule 52, which contains a protease activating solution. First receptacle 46 and second receptacle 50 are in fluid communication with a mixing chamber 54, which serves for providing fluid contact and mixing of the contents of first reservoir 48 and second reservoir 52, activating the stabilized, inactivated protease. A mixer 12 as described above can be placed within mixing chamber 54.

In another embodiment, illustrated in FIG. 7, first receptacle 58 receives first modular reservoir or ampoule 60, which contains stabilized, inactive, protease preparation in powder, lyophilized and/or other non-aqueous form. Second receptacle 62 receives second modular reservoir or ampoule 64, which contains the activating solution. First receptacle 58 and second receptacle 62 are in fluid communication with mixing mechanism 56, providing contact between and effect dispersal of the non-aqueous protease preparation in the activating solution.

The ability of proteases to gently disrupt the integrity of dermal tissue has led to the therapeutic use of proteolytic enzymes as an adjunct, or alternative to mechanical or laser surgical treatment of skin lesions. In order for such enzymatic treatment to overcome the abovementioned disadvantages of surgical, electrosurgical, cryosurgical and laser-surgical methods (pain, scarring, traumatic stress, hyperpigmentation and destruction of neighboring tissue), it is desirable for the proteolytic method to readily and thoroughly hydrolyze a wide variety of proteins found in skin lesions; function at physiological pH and temperature; be compatible with adjunct therapies (e.g., anesthetics, cleansing agents, topical antibiotics); and not interfere with normal wound healing or complicate skin grafting. In addition, it is important to provide means of retention and preservation of the viability of the isolated, removed cells for histological examination or cell culture; to allow for localized and confined application of the protease and provide for stability of the enzyme formulations from the effects of pH, temperature and autoproteolysis. These and other beneficial considerations are addressed, for the first time in an integrative approach, by the present invention. Thus, benefits provided by the present invention include gentle enzymatic tissue removal enhanced by mechanical "stripping" action of the locally directed protease stream, superior pain reduction and wound healing provided by inclusion of anesthetics, coagulants/anticoagulants and antibiotics in the protease solution and availability of removed skin cells for histological examination and/or cell culture from the treated lesions. In addition, control of temperature, ph and flow rate of the stream of protease solution, and provision for on-site activation of stabilized enzyme preparations ensure delivery of accurate, effective levels of catalytic activity, to the lesion surface.

Proteases are widely applied in the debridement of non-viable tissue, for example, as described by Mekkes, J. R. et al. (same as above); conditioning of skin imaged by $CO_2$ laser surgery, for example, as described by Gaspar, L. et al. (same as above); and aging, for example, as disclosed in U.S. Pat. No. 5,976,556 to Norton, et al., exploiting the ability of the enzyme to digest protein components of extracellular matrix without damaging healthy tissue. The choice of suitable enzyme preparations, methods of application, and extent of treatment have emphasized the removal of debris and non-viable tissue. Since collagen, elastin, fibrinin and proteoglycan predominate in the skin's extracellular matrix, and are of even greater significance in abnormal conditions such as keloids, scars, warts and fibroses, enzymes of the type collagenase, elastase and hyaluronidase, and combinations thereof, have been most often employed for treatment of dermatological lesions. However, the methods of treatment with these enzymes have been limited to topical application and intradermal injection.

Thus, Pinnell, in U.S. Pat. No. 4,645,668, teaches the treatment and prevention of acne and hypertrophic scars, keloids, wrinkles and cellulite with repeated intradermal injections of proteases, principally collagenase, with additional hyaluronidase. The author achieved significant resolution of most of the lesions treated, indicating the efficacy of protease digestion of matrix tissue, and reported few, if any, negative effects. However, repeated intradermal injections, over a period of weeks, were required to achieve the desired effects. In addition to the discomfort and protracted character of such a treatment regimen, no retention of cells from the lesions is made possible, necessitating conventional, surgical biopsy methods prior to enzymatic treatment. Similarly, de Faire et al. in U.S. Pat. No. 5,958,406, teach the treatment of a variety of conditions associated with cell-adhesion related processes with multifunctional enzyme krill protease, comprising chymotrypsin, trypsin, elastase, collagenase and exo-peptidase activity. Treatment of dermal and internal lesions is addressed, by topical, parenteral, aerosol, systemic, intramuscular and intradermal delivery of the protease compositions. Intradermal injection of proteases is recommended for treatments of scar and keloid lesions. Thus, cell collection or retention from the treated area is not possible and, as in other dermatological enzyme treatment protocols, no control of protease activity after administration is afforded.

Topical application, or injection of proteases offers little control over the level of catalytic activity remaining in situ, with autoproteolytic and normal dermal lytic and acidic processes causing unpredictable degradation. Although many protocols for topical or intradermal delivery of proteases depend on individual, empirical results for determining duration of treatment, it has been suggested that topical treatment application of acid proteases, compatible with the normal pH of human skin, can ensure greater control over active enzyme dosage, as described in U.S. Pat. No. 5,976,556 to Norton et al. However, in the aforementioned invention, as with other topical protease applications, there remains no ongoing control of enzyme activity post treatment.

Thus, according to one aspect of the present invention, there is provided a method of removing cells from a skin portion of a subject inflicted with a dermatological lesion, the method effected by streaming a solution containing an effective amount of at least one protease, over, and in contact with, the skin portion, thereby removing the cells from the skin portion of the subject. By combining enzymatic digestion of intracellular matrix proteins and mechanical disruption of the lesion surface by a fluid force, cells of the treated skin portion become dislodged and may be removed by the stream of at least one protease solution. Non-enzymatic debridement, employing a topical preparation comprising tannic acid and aloe vera has been proposed for treatment of lesions such as keratoses, freckles, dermal ulcers, papilloma, blemishes and benign nevi, as disclosed in U.S. Pat. No. 5,420,114 to Clodman et al. Furthermore, application of the protease solution via streaming onto the lesion surface affords precise localization and control of magnitude and duration of enzymatic activity, through manipulation of enzyme concentrations, pH, temperature, hydrophobicity/hydrophilicity of the enzyme solutions, intensity of streaming, duration and site of contact with protease solution throughout treatment. As described above, enzymatic surgery device 80 of the present invention provides such diverse control of protease treatment through, for example mixer 12, thermoregulator 14, pump 18 and applicator 24.

As used herein, the term "protease" refers to any biologically active molecule, typically a polypeptide, possessing enzymatic peptide hydrolase activity, including endopeptidase and/or exopeptidase activity.

In one preferred embodiment of the present invention, the protease is, but not limited to, vibriolysin, krill protease, chymotrypsin, trypsin, collagenase, elastase, dipase, proteinase K, *Clostridium* multifunctional protease and *Bacillus subtillis* protease. These represent proteases commonly employed in therapeutic methods, have demonstrated low incidence of undesirable side effects, and are commercially available in pure, purified or genetically engineered form, for example, Esperase, Subtilisin A, Savinase, and Durazyme, available from Novo Nordisk Bioindustry Japan K.K.; Protease N "Amano", Protease S "Amano", available from Amano Pharmaceutical K.K.; Bioprase, available from Nagase Seikagaku Kogyo K.K.; and Purified Collagenase, available from Advance Biofactures, Lynbrook, N.Y.

*Clostridium* multifunctional protease and krill protease are easily prepared by one skilled in the art, for example, as disclosed in U.S. Pat. No. 6,416,626 to Markert et al., and U.S. Pat. No. 5,958,406 to de Faire et al., respectively.

Other proteases which may be selected are papain, bromelain, plasminogen activator, plasmin, mast cell protease, lysosomal hydrolase, streptokinase, pepsin, and any or all fungal, bacterial, plant or animal proteases. The protease solution of the present invention may contain a single protease, or, preferably, a plurality of proteases. The protease solution may also contain one or more glycosaminoglycans degrading enzyme, such as, but not limited to, various lysosomal hydrolases which include certain endoglycosidases (heparanase and CTAP degrade heparan sulfate and to a lesser extent heparin, and hyaluronidase from sheep or bovine testes degrade hyaluronic acid and chondroitin sulfate), various exoglycosidases (e.g., β-glucoronidase), and sulfatases (iduronate sulfatase), generally acting in sequence to degrade the various glucosaminoglycans. Bacterial lyases such as heparinase I, II and III from *Flavobacteriun heparinum* cleave heparin-like molecules, chondroitinase ABC from *Proteus vulgaris*, AC from *Arthrobacter aurescens* or *Flavobacterium heparin*, B and C from *Flavobacterium heparin* degrade chondroitin sulfate.

Conventional mechanical and non-mechanical methods of treating and removal of skin lesions such as razor-blade or scalpel excision, $CO_2$ laser surgery, cryosurgery, electrocauterization, and electroablation are associated with pain, stress trauma, bleeding, scarring, contamination, hyperpigmentation and disruption of adjacent and underlying tissue. The milder proteolytic digestion of skin lesions and wounds has been shown to provide superior healing of such lesions, with decreased incidence of scarring, bleeding and contamination. Indeed, protease preparations are commonly used to promote healing and reduce the scarring of $CO_2$ laser surgery wounds (4).

Of even greater advantage, then, is the combination of additional topical, non-protease substances capable of reducing undesirable side effects. Schmitt et al. in U.S. Pat. No. 4,122,158, teaches the application of a biopolymer comprising protease, antibacterial, antibiotic and antifungal substances for the treatment and prevention of scarring and contamination in burn wounds. Even the mild degrees of bleeding, pain and scarring potentially associated with enzymatic removal of cells from skin lesions can be alleviated by application of suitable substances simultaneously with the protease solution. The enzyme surgery device 80 of the present invention is well suited for delivering solutions containing additional active substances compatible with the protease activity, either through their inclusion in the solution or protease in first reservoir 10, second reservoir 34 or 38, third reservoir 36, reservoir or ampoule 44, first reservoir or ampoule 48, second reservoir 52, first reservoir or ampoule 60, and/or second reservoir or ampoule 64. Thus, in a further, preferred embodiment of the present invention, the protease solution contains at least one of a local anesthetic, a coagulant and an anticoagulant. In yet another embodiment, the protease solution further contains an effective amount of an antibiotic.

As used herein, the phrase "local anesthetic" refers to any agent applied within a proscribed region (e.g., not systemically) effecting significant reduction or inhibition of activity of nonciceptive substances, receptors and/or neural pathways. Non-limiting examples of commonly used local anesthetic agents are cyclo-oxygenase inhibitors (e. g. ibuprofen, indomethacin and ketorolac), 5-hydroxytryptamine receptor antagonists (e.g. amytryptyline), bradykinine receptor antagonists and histamine receptor antagonists.

As used herein, an "effective amount" of antibiotic is intended to include the amount of antibiotic sufficient to significantly prevent and inhibit at least 50%, preferably 75% and most preferably 100% of microbial growth within a dermatological lesion of the subject being treated, such effective amount determined by one skilled in the art.

Preconditioning of the dermatological lesion surface may provide superior efficiency of subsequent protease treatment. Normal epidermis consists of layers of dead squamous cells which provide an effective mechanical barrier protecting the underlying viable dermal layers. Yu et al (U.S. Pat. Nos. 4,105,783 and 4,363,815) describe removal of dead cells from the keratin-rich stratum corneum with keratinolytic, desquamifying agent such as low molecular weight hydroxy or keto acids, and their esters. Such exfoliation of the skin is also achieved by cosmetic preparations containing dermabrasives, emollients, detergents, astringents and skin softeners. Thus, in a yet further embodiment of the present invention the surface of the lesion is pretreated by streaming of cleansing, softening, astringent, exfoliating and or dermabrasive agents. Device 80 is well suited for this application, requiring only the provision of a suitable pretreatment solution in first reservoir 10, second reservoir 34 or 38, third reservoir 36, reservoir or ampoule 44, first reservoir or ampoule 48, second reservoir 52, first reservoir or ampoule 60, and/or second reservoir or ampoule 64.

It will be appreciated, in the context of the present invention, that autolysis and loss of functional enzyme concentration from catalytically active preparations of proteases constitutes a significant disadvantage of therapeutic administration of enzymes in topical, injected and/or other compositions. Active shelf life of the protease is limited, and precise control of enzyme activity at the site of administration is virtually unattainable, once injection or topical application is completed. A number of inventions have proposed the storage of biologically active substances, including enzymes, in contact with substances or under conditions limiting their native activity, effectively inactivation and stabilization, until contacted with substantially adequate amount of activating substance, or conditions sufficient to restore biological activity. For example, Edens, et al (U.S. Pat. No. 6,117,433) teach the stabilization of biologically active substances, such as vitamins, enzymes and antibiotics in high concentrations by preparation in water activity lowering agents such as salts, polyols, sequestering agents such as EDTA, phyate or gluconate, or antioxidants such as sulphites, glutathione, cysteine or ascorbic acid. Crystallized compositions of biologically active substances, typically more stable than aqueous preparations, are mixed with viscosifying agents to retard precipitation and ensure homogeneity of the biologically active composition. The disclosure further describes a dispensing system for such stabilized formulations, activating the biologically active substance by dilution with an aqueous composition. Nakagawa et al. in U.S. Pat. No. 5,409,546 describes the stabilization of *Vibrio* protease for contact lens cleanser composition by addition of polyols, and the specification of a defined range of temperatures (room temperature to about 58° C.) within which the enzyme retains catalytic activity. Rowan et al. in U.S. Pat. No. 5,106,621 teaches the restoration of catalytic activity of a plant cysteine protease for treatment of burn wounds by addition of cysteine for regeneration of thiol groups. None of the aforementioned examples, however, relate to the administration of proteases for treatment of living cells, nor provide for ongoing, precise control of the activation of catalytic activity at the site of application.

Thus, in a preferred embodiment of the present invention, the protease is activated shortly prior to streaming the solution containing the effective amount of the at least one protease, over, and in contact with, the treated skin portion. The method wherein the protease is activated may be effected by: (a) keeping the protease at a first temperature in which the protease is substantially catalytically inactive and heating and/or cooling the at least one protease to a second temperature in which the at least one protease is catalytically active; and/or (b) providing the protease in a powder form and mixing the powder with a solution in which the protease is catalytically active; and/or (c) providing the protease in a first solution in which the protease is substantially catalytically inactive and mixing the first solution with a second solution so as to achieve a mixed solution in which the protease is catalytically active. The second solution may differ from the first solution with respect to pH, ion concentration, free metal concentration, hydrophilicity and hydrophobicity. For example, FIG. 1 depicts enzymatic surgery device 80 in fluid communication with thermoregulator 14, enabling filling of first reservoir 10 with protease solution at sub-optimal, stabilizing temperatures, restoring catalytic activity by raising the temperature of the protease solution only shortly prior to application at the lesion site. Typically, enzymes are substantially inactivated at temperatures below 10° C., preferably 4° C. Activation of enzyme catalytic activity may be accomplished by heating and/or cooling the protease solution to optimal temperature, typically in the range of 30 to 40° C., preferably 37° C.

As used herein, the term "hydrophilicity" refers to the polar nature of a solution or compound, indicating its tendency to be attracted to other solutions or compounds exhibiting significant dipole moments. Likewise, the term "hydrophobicity" refers to the non-polar nature of a compound or solution, indicating its tendency to be repelled by and immiscible in other compound or solutions exhibiting significant dipole moments.

As used herein, the term "inactivation" refers to the reversible or irreversible suppression or loss of catalytic activity, for example, inactivation rendering proteolytic enzymes incapable of catalyzing hydrolysis of peptide bonds.

In the context of the present invention, it will be appreciated that many enzymes are designated as acid, neutral or basic, according to the physiological environment to which they are adapted. For example, the digestive enzymes pepsin and chymotrypsin, catalytically active in the acidic environment of stomach, exhibit low (pH 3–5) pH optima. Enzymes active in the environment of the dermis will typically have pH optima closer to the milder, acid mantle of the skin (pH 5.5–6.5). Thus, autolysis of the protease of the present invention may be inhibited prior to application by maintaining the protease at a non-optimal pH, and mixing the enzyme solution with an activating solution effectively achieving optimal pH shortly prior to administration to the treated lesion. Thus, in one preferred embodiment of the present invention, as illustrated in FIGS. 3 and 6, inactive stabilized protease solutions in second reservoir 34 and/or first reservoir or ampoule 48 are prepared in non-optimal pH, and the activating solution of third reservoir 36 and/or second reservoir or ampoule 52 restores optimal pH for catalytic activity upon mixing shortly prior to administration to the treated lesion. Most preferably, a pH optimum for catalytic activity is chosen which approximates the mildly acidic normal pH of mammalian skin. Similarly, protease solutions may be inactivated and stabilized by chelation of catalytically critical metal ions such as $Ca^{++}$ or $Mg^{++}$, with EDTA, for example. Activation may be then achieved by providing a concentration of the critical metal ion in the activating solution sufficient to achieve effective and/or optimal metal ion concentrations after mixing. Alternatively, or additionally, proteases may be stabilized and inactivated by preparation in solutions of reduced water availability, as in high salt and polyol concentrations, for example. Restoration of catalytic activity, shortly prior to streaming of the protease solution at the site of treatment, is accomplished by sufficient aqueous dilution by the activating solution. In the context of the present invention, it should be noted that enzymes extracted from different species (i.e., marine, thermophilic, halophilic, euthermic, mammalian, cryophilic, etc.) often demonstrate widely variable and species specific optima of pH, temperature, metal prosthetic group and ion concentration, and polar interactions (hydrophobicity/hydrophilicity).

In one preferred embodiment of the present invention, protease is provided in a non-fluid, powder form, mixing with an activating solution shortly prior to application to achieve catalytic activity. The viability of dried enzyme preparations is well know in the art, and many proteases of excellent grades of purity are commercially available in lyophilized form, for example Proteinase K (Sigma-Aldrich, Israel), Clostridopeptidase A (Sigma-Aldrich) and Elastase (Fluka Chemical Company Inc.). However, powdered, lyophilized or granulated enzyme preparations are often difficult to disperse homogeneously in diluent solutions. Thus, in one preferred embodiment of the present invention, illustrated in FIG. 4, powdered or lyophilized protease preparation(s) are held in first reservoir 10, contacted and mixed to homogenieity with activating solution from second reservoir 38 in mixer 12 shortly prior to delivery at the treatment site. In another embodiment described in detail above and illustrated in FIG. 7, the powdered or lyophilized inactivated protease is provided in separate reservoir or ampoule 60 and is contacted with, and dispersed in, the activating solution, provided in reservoir or ampoule 64, by the action of mixing mechanism 56 shortly prior to delivery at the treatment site. Thus, the method of the present invention incorporates the advantages of stabilized, non-aqueous powdered or lyophilized protege preparations while avoiding the disadvantages of poor dispersal in diluents and imprecise control of enzyme active at delivery.

It will be appreciated, in the context of the present invention, that catalytic activity of enzymes may be modified by activators and inhibitors. One such mode of regulation of enzyme activity is reversible inhibition, effected by the interaction of substrate analogs or regulatory molecules which cause changes in substrate binding and/or enzyme kinetics, effectively reducing catalytic activity, for example, as described in "Enzymes", chapter 3, in Molecular Cell Biology (1986): Darnell, J, Lodish, H and Baltimore, D, eds., Scientific American Books, Inc. Since such reversible inhibition of enzyme activity is concentration dependent, restoration of catalytic activity is achieved by contacting the inhibited enzyme preparation with appropriate volumes of diluent devoid of inhibitors. Thus, in a further embodiment of the present invention, stabilization of the protease solution is effected by the inclusion of an effective amount of reversible enzyme inhibitor(s). Activation of the stabilized protease preparation is effected by dilution with adequate volumes of activating solution devoid of inhibitor/and or inhibitor activity.

Similarly, the device and methods of the present invention provide for precise and accurate control of termination of enzymatic activity at the site of treatment and in the collected cells. Inactivation of protease activity effected by manipulation any of the aforementioned methods (pH, ion concentration, free metal concentration, hydrophilicity/hydrophobicity, water availability and reversible inhibition) may be effected by following protease streaming with application of effective amounts of protease-free solution(s) containing, for example, metal chelators, buffers of non-optimal pH and reversible protease inhibitors.

In the context of the present invention, it will be appreciated that many dermatological lesions contain abnormal skin cells and intracellular matrix. For example, psoriatic plaques are caused by abnormal epithelial cell turnover, the collagen of keloids and hypertrophic scars is characterized by abnormal crosslinking, warts are the result of papovaviral infection of epidermal cells, and various types of often hyperpigmented, hyperplastic cells comprise the many types of nevi (moles), keratoses and lentigines. Whereas proteolytic disruption of the intracellular matrix with subsequent resorption of the non-viable tissue has been the objective of previous enzymatic methods, in the present invention the abnormal cells of dermatological lesions are removed, effecting a superior treatment of these skin conditions. Thus, in one preferred embodiment of the present invention controlled streaming of protease solution may be administered to treat conditions of the skin surface including, but not limited to warts, lentigines, melasmas, acne, keratoses, nevi, keloids, hypertrophic scars, psoriasis and tattoos.

It will be appreciated that the combination of mechanical "stripping" and enzymatic action of a stream of protease solution on the skin surface is suitable for removal of skin cells and debris for esthetic purposes. Thus, in a further embodiment of the present invention, controlled streaming of a protease solution may be used to cosmetically treat esthetically undesirable portions of the skin surface.

The methods and device of the present invention may also be applied for the treatment and/or removal of cells from the surface of tissue within a patient, or of internal tissues temporarily exposed during surgical procedures. Markert et al. (U.S. Pat. No. 6,146,626) describe the harvesting of cells for tissue culture from internal organs including liver, spleen, heart and skeletal muscle, connective and nerve tissue, glandular tissue, endothelium and others effected by digestion with *Clostridium* collagenase and elastase enzymes. De Faire et al. (U.S. Pat. No. 5,958,406) describe the treatment and prevention of infection in internal organs and body cavities by the injection or application of preparations containing krill multifunctional protease activity.

According to a further aspect of the present invention there is provided a method of removing and collecting cells from a surface of a viable tissue, the method is effected by streaming a solution containing an effective amount of at least one protease, over, and in contact with, the surface, thereby removing cells from the surface of the viable tissue, and collecting the cells. In one preferred embodiment of this aspect of the present invention the streaming of protease solution is applied to the tissue surface via an open surgical incision. In another, more preferred embodiment the device and method of the present invention are employed to provide protease irrigation, removal and/or sampling for biopsy of a tissue surface or surfaces via the abovementioned "push-pull" cannula in a closed, fiber optic-directed surgical procedure. Non-limiting examples of such procedures are arthroscopy, cystoscopy, endoscopy, cholecystoscopy, laparoscopy, colonoscopy, and myringoscopy.

As used herein, the term "treatment" includes the diminishment or alleviation of at least one symptom associated or caused by the disorder being treated. For example, treatment can be diminishment of several symptoms of a disorder or complete eradication of a disorder.

The importance of obtaining cells from dermatological lesions cannot be overstated. Treatment without determining accurate diagnosis may remove the lesion, but will often incur unnecessary scarring, recurrences, and financial hardships. Of particular importance is the determination of cells type(s) comprising nevi and keratoses, due to the widespread prevalence of these lesions in adults, and their potential for malignant transformation (Sosis, A., Benign Tumors of the Skin, in Skin Diseases: Diagnosis and Management in Clinical Practice (1982), Binnick, S. A. ed, Addison-Wesley Publishing Co., USA. 166–230). As mentioned above, previous methods of non-surgical treatment of skin lesions, such as laser surgery, electrosurgery and chemical or enzymatic ablation have not provided any means for obtaining cells from the lesions, necessitating the use of traditional surgical biopsy techniques for accurate diagnosis.

Figure 2:
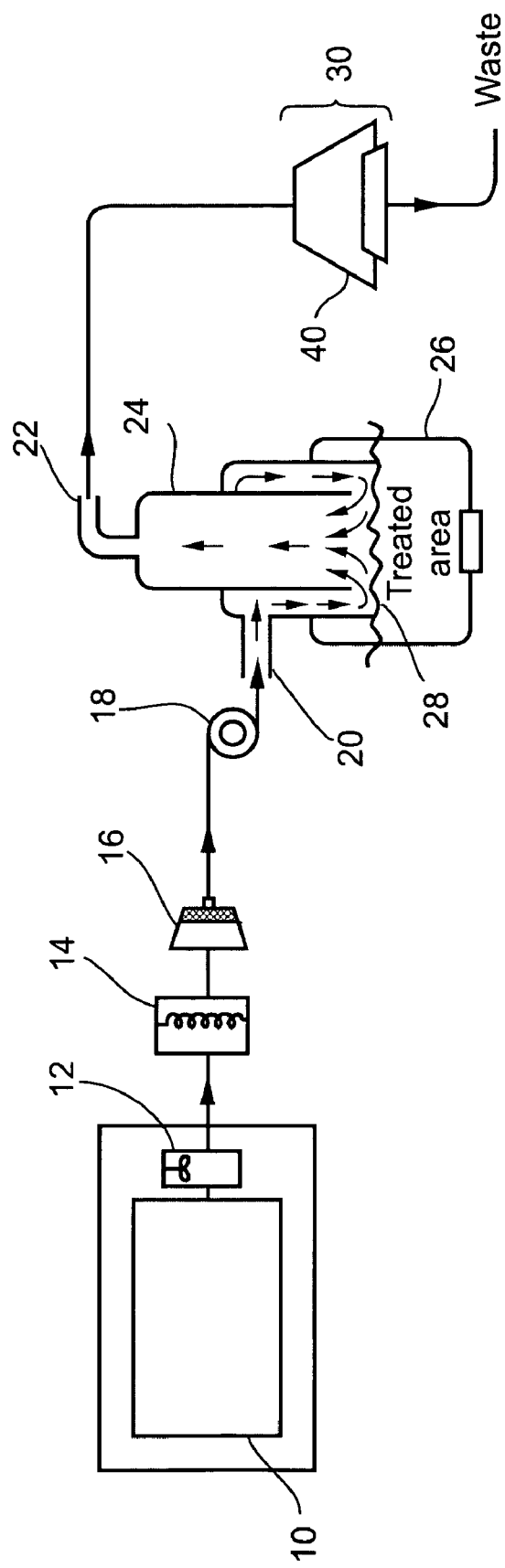
FIG. 2 is a cross-sectional view of a device in accordance with another embodiment of the present invention.

In the context of the present invention, it will be appreciated that confining the enzymatic activity to a stream of protease solution directed at the lesion surface, rather than topical application of creams or intradermal injection, provides the opportunity for retention of the cells removed from the treated lesion. Thus, according to another aspect of the present invention, there is provided a method of removing and collecting cells from a skin portion of a subject inflicted with a dermatological lesion, the method effected by streaming a solution containing an effective amount of at least one protease, over, and in contact with, the skin portion, thereby removing the cells from the skin portion of the subject; and collecting the cells. The products of protease digestion at the site of treatment, the site defined by the perimeter of skin-facing surface 28 of applicator 24, are removed through outflow port 22, and are transferred to cell collector 30, in fluid communication with applicator 24. Separation of tie fluid and cellular components of the outflow of protease solution from applicator 24 may be accomplished by filtration, or, in another embodiment, by continuous flow centrifugation, as described above. Small volume continuous flow centrifuges, commonly used for separation of blood components (for example, the OrthoPAT® System, Haemonetics Corporation, Braintree, Mass.) are commercially available and are easily adapted to the device of the present invention through fluid communication, as illustrated in FIG. 2. Alternatively, cell collection may be effected by retention on a column capable of adsorbing cells through interaction with proteinaceous, poly- and/or oligo saccharide or other cell-surface components.

Known cell separations involve several techniques, some of which are based on specific affinities. Other cell separation techniques rely on more serendipitous mechanisms such as entrapment of target cells in supports of various origins and structures. See, for example, Wigzell and Anderson, J. Exp. Med. 129:23–36, 1969; Rutishauser et al. Proc. Natl. Acad. Sci. 70, 1973; Wysocki and Sato, Proc. Natl. Acad. Sci. 75:2844–2848, 1978; Antoine et al. Immunochem. 15, 1987. See also, U.S. Pat. No. 6,008,040 to Datar. The basic process of affinity separation entails creating contact between cell mixtures to be separated and a support matrix to enable the target cells to preferentially attach, bind, adsorb or become trapped to and within the support, and then washing away the undesired cells, or vice versa. Specific affinity techniques use monoclonal antibodies to recognize specific markers on the membranes of cells and to "attract" the target cells to bind to the monoclonal antibodies. Specific affinity "attractions" of target cells also may occur by hydrophobic or hydrophilic interactions, metal-affinities, ion exchangers, and the like. Thus, in a further embodiment of the present invention, cell collection is effected by passage of the outflow stream from applicator 24 through cell collector 30 and contacting with a device, e.g. a cell-binding column, capable of retention of the cells and their separation from the outflow stream.

According to another aspect of the present invention, there is provided a composition comprising at least one protease and at least one substance selected from: a local anesthetic, a coagulant and an anti-coagulant. According to yet another aspect of the present invention, there is provided a pharmaceutical composition comprising a pharmaceutically acceptable carrier and, as active ingredients, at least one protease and one or more of the following: a local anesthetic, a coagulant and an anti-coagulant. In one embodiment of the present invention, the composition fiber contains an effective amount of an antibiotic.

As used herein, the term "coagulant" is defined as any agent that promotes clotting, or coagulation of blood, which may be safety applied to a dermatological lesion. A non-limiting example of such a coagulant material comprising gelatin, thrombin and calcium is described in U.S. Pat. No. 6,045,570 to Epstein, et al. Likewise, the term "anti-coagulant" refers to any agent which retards, inhibits or prevents the clotting or coagulation of blood, which may be safely applied to a dermatogical lesion, such as heparins, coumarins or other agents possessing thrombolytic activity.

The language "effective amount" is intended to include the amount of the at least one protease sufficient to remove or significantly reduce progression of a dermatological lesion of the subject being treated. An effective amount can be determined on an individual basis and will be based, at least in part, on consideration of the severity of the symptoms to be treated and the activity of the specific protease selected. Thus, an effective amount of the at least one protease can be determined by one of ordinary skill in the art employing such factors as described above using no more than routine experimentation in health care management.

As used herein in the specification and in the claims section below, the phrase "pharmaceutically acceptable carrier" refers to a pharmaceutically acceptable material, composition or vehicle, such as a liquid filter, diluent, solvent or encapsulating material, involved in carrying or transporting a compound(s) of the present invention within or to the subject such that it can perform its intended function. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; fruit acids, pyrogen-free water; isotonic saline; Ringer's solution; ethyl alcohol; phosphate buffer solutions; and other non-toxic compatible substances employed in pharmaceutical formulations.

The pharmaceutical compositions of the present invention formulated as solutions typically include a pharmaceutically-acceptable aqueous or organic solvent. The phrases "pharmaceutically-acceptable aqueous solvent" and "pharmaceutically-acceptable organic solvent" refer to a solvent that is capable of having dispersed or dissolved therein the active compound, and possesses acceptable safety properties (e.g., irritation and sensitization characteristics). Water is a typical aqueous solvent. Examples of suitable organic solvents include: propylene glycol, butylene glycol, polyethylene glycol (200-600), polypropylene glycol (425-2025), glycerol, 1,2,4-butanetriol, sorbitol esters, 1,2,-6-hexanetriol, ethanol, isopropanol, butanediol, and mixtures thereof. Preferably, these solutions contain from about 0.01% to about 50% of the active compound, more preferably from about 0.1% to about 20%; and from about 1% to about 80% of an acceptable aqueous or organic solvent, more preferably from about 1% to about 40%.

Additional objects, advantages, and novel features of the present invention will become apparent to one ordinarily skilled in the art upon examination of the following example, which is not intended to be limiting. Additionally, each of the various embodiments and aspects of the present invention as illustratively described hereinabove and as claimed in the claims section below finds experimental support in the following example.

EXAMPLE 1

Enzymatic Epidermis Removal

Design and fabrication of an applicator for the treatment of skin surface area 9 mm in diameter: An applicator for the treatment of skin areas, 9 mm in diameter, was configured as illustrated in FIG. 10. The applicator was fabricated in a workshop with special emphasis on making the skin contacting surface from silicone to ensure flexibility and effective sealing.

Reference is now made to FIG. 10, which is a cross sectional view of an exemplary specific preferred embodiment of applicator 24 for practicing the present invention on skin. Applicator 24 includes a body member in the form of housing 100 having an inlet 102 and an outlet 104. Fluid entering through inlet 102 is directed via a first tube structure or conduit 106 to a treatment zone 107 defined by a somewhat conical silicon structure or skirt 114 having an out-turned rim defining a skin-facing opening 108, 9 mm in diameter. A second tube structure or conduit 110 positioned within first tube structure 106 is used to direct fluid from treatment zone 107 to outlet 104. An O-ring 112 is used to restrict flow to the intended direction within first tube structure 106. As seen in FIG. 10, silicon elastomer skirt 114 is fixed to a head 116 threadably mounted on the open end of housing 100, and is of decreasing diameter towards its out-turned rim. This head or screw mechanism 116 allows adjustment of the height of opening 118 of second tube structure 110 with respect to skin-facing opening 108 of treatment zone 107. Head 116 may be threaded within the open end of housing 100 to permit axial adjustment of the distance between the skin-facing opening 108 of skirt 114, and the open end of conduit 118 communicating with the outlet 104. The arrangement is such that the out-turned rim of the silicon skirt 114, when brought into contact with the skin to be treated defines a confined space with that surface, with the annular space between silicon skirt 114 of housing 100 and conduit 110 defining a first passageway between that confined space and inlet port 102, and with the interior of conduit 110 defining a second passageway between the confined space and the outlet port 114. The annular skirt 114 enables the open end of the housing to conform to irregularities in the surface of the skin to be treated, and the threaded mounting of head 116 enables the open end of the housing to accommodate irregularities in the surface of the skin to be treated. Preferably, a pump, as illustratively described hereinabove, is used to direct fluid from a reservoir into inlet 102. A drainage tube is used to drain fluid from outlet 104.

Enzymatic epidermis removal: Using the applicator 24 illustrated in FIG. 10, an enzyme solution containing Collagenase (1 mg/ml, Sigma Cat. No. C0130) and Thermolysin (0.5 mg/ml, Sigma type x, Cat No. P1512) in 0.1 M PBS buffer, pH 7.5, was applied onto a skin sample freshly removed from an adult female large-white (1 year old, 90 kg) pig, mounted on a flat holder and pre-cleaned with 70% (v/v) aqueous ethanol, at a flow rate of 3–4 ml/hour for 3 hours at room temperature.

Figure 11A:
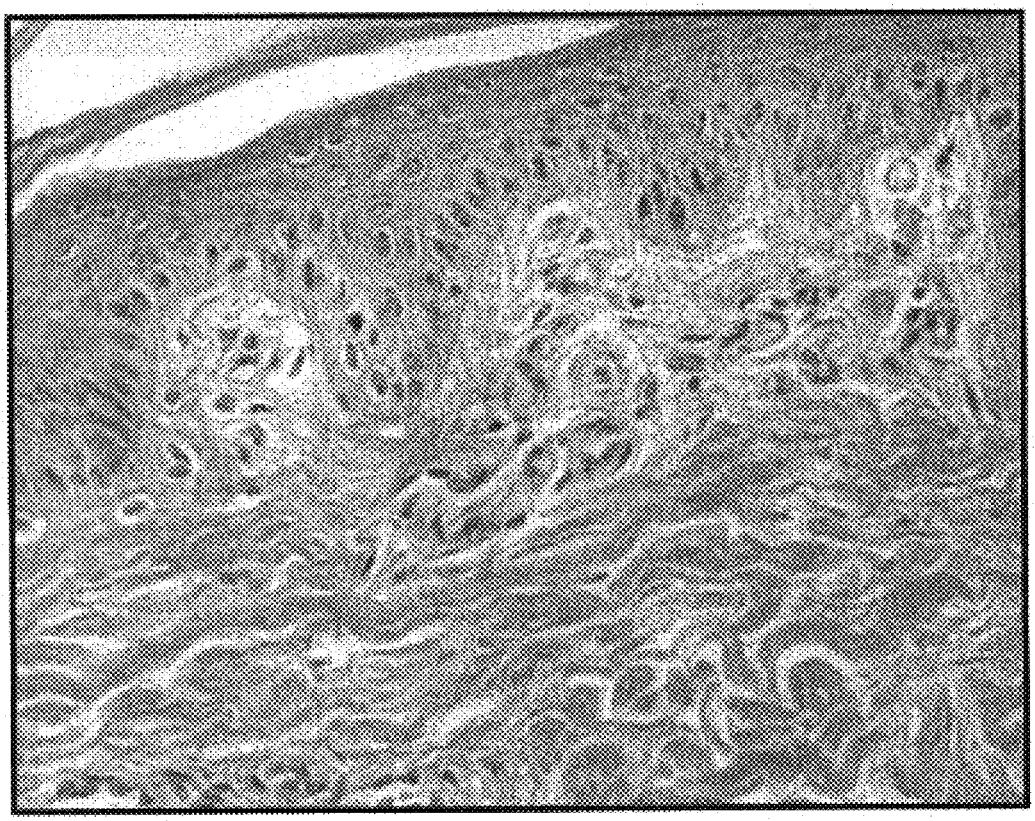
FIGS. 11A–11B are photographs of histological section of untreated pig skin and pig skin treated with a stream of proteolytic enzymes using the applicator device of FIG. 10, according to the present invention.
Figure 11B:
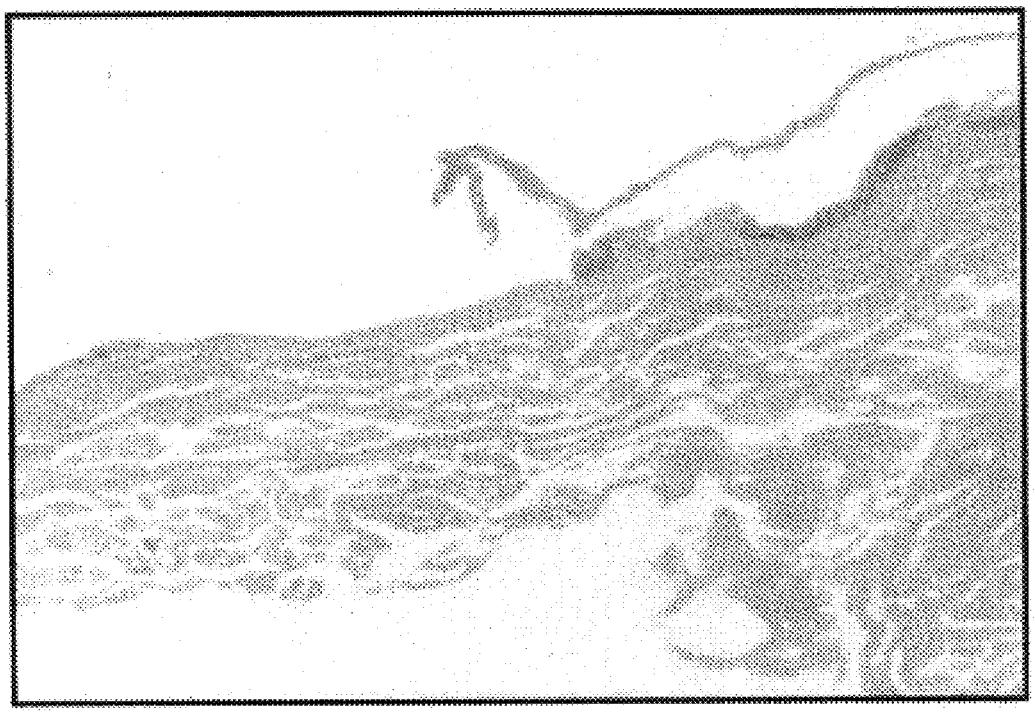

Following this treatment and detouchment of the applicator-device, complete hair removal from the treated area, accompanied by the formation of smooth, crater like removal of skin volume was macroscopically observed. The skin sample was immediately fixed in neutral buffered fornalin (4% v/v) for 48 hours. The skin was then rinsed with distilled water, dehydrated in alcohol and embedded in paraffin. Stained histological serial sections (0.8 µm in thickness) were then prepared in a plane parallel to the Epidermis-Dermis direction, mounted on slides, stained with Hematoxilin-Eosin and examined under light microscope. Examination of the edges of the treated area clearly indicated enzymatic epidermis removal from the treated area (FIG. 11B) as compared to untreated skin (FIG. 11A).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An applicator for applying a solution containing an effective amount of at least one protease to a skin portion of a subject for treatment thereof, comprising:

a body member having an open end defining an annular surface to be brought into contact with the skin portion to thereby define a confined space therewith;

at least one inlet into the body member communicating with the confined space via a first passageway for applying the protease solution to the skin portion within the confined space;

at least one outlet from the body member communicating with the confined space via a second passageway through the body member for outletting therefrom the protease solution after applied to the surface of the object within the confined space; and a source of the protease solution to be inletted via the inlet and to be streamed into and out of contact with the skin portion of the subject for enzymatically and mechanically removing cells therefrom.

2. The applicator of claim 1, wherein the body member is a housing having an open end mounting a head carrying a flexible skirt of plastic material formed with an annular rim to contact the skin portion to be treated; the head being threadedly mounted on the housing to permit axial adjustment of the distance between the annular rim of the skirt, and at least one of the passageways, to accommodate irregularities in the surface of the skin portion to be treated.

3. The applicator of claim 2, wherein the flexible skirt is of conical configuration, and the annular rim is an out-turned rim to enhance its contact with the surface of the skin portion to be treated.

4. The application of claim 1, wherein the body member includes a conduit extending through the body member; the conduit having an open end in the confined space, and an opposite end communicating with the inlet or outlet such that the interior of the conduit defines one of the passageways, and an annular space between the conduit and the body member defines the other of the passageways.

5. The applicator of claim 4, wherein the opposite end of the conduit communicates with the outlet such that the interior of the conduit defines the second passageway communicating with the outlet, and the annular space between the conduit and the body member defines the first passageway communicating with the inlet port.

6. The applicator of claim 1, wherein the applicator further comprises a collector communicating with the outlet port for collecting the solution after contact with the skin portion to be treated, and for separating from the solution cells removed from the skin portion by the solution.

7. The applicator of claim 1, wherein the applicator further comprises a heater or cooler for heating or cooling the protease solution before inletted into the inlet.

8. The applicator of claim 1, wherein the applicator further comprises a cell collector communicating with the outlet for collecting the protease solution after streamed into and out of contact with the skin, and for separating therefrom the cells removed from the skin.

9. The applicator of claim 1, wherein the source comprises a first reservoir in fluid communication with the at least one inlet, the first reservoir containing the protease solution.

10. The applicator of claim 9, further comprising a pump that is operatively connected between the first reservoir and the at least one inlet for effecting the streaming of the solution in the first reservoir to the at least one inlet.

11. The applicator of claim 9, wherein the first reservoir is arranged to direct, by gravitation, the solution towards the at least one inlet.

12. The applicator of claim 9, further comprising a thermoregulator that is operatively connected between the first reservoir and the at least one inlet.

13. The applicator of claim 9, further comprising a mixer that is operatively connected between the first reservoir and the at least one inlet.

14. The applicator of claim 9, further comprising a filter that is operatively connected to the first reservoir and the at least one inlet.

15. The applicator of claim 9, further comprising a cell collector that is operatively connected to the at least one outlet, wherein the collector is arranged to receive the solution and the removed cells, cellular debris and tissue debris from the inlet.

16. The applicator of claim 15, wherein the cell collector further comprises a filter for collecting the removed cells from the skin portion of the subject.

17. The applicator of claim 15, wherein the cell collector further comprises a continuous flow centrifuge for collecting the removed cells from the skin portion of the subject.

18. The applicator of claim 9, wherein the first reservoir contains the protease solution wherein the at least one protease is substantially catalytically inactive.

19. The applicator of claim 18, wherein the solution contains at least one protease selected from the group consisting of papai, bromelain, vibriolysin, krill protease, chymotrypsin, trypsin, collagenase, elastase, dipase, proteinase K, *Clostridium* multifunctional protease and *Bacillus subtilis* protease.

20. The applicator of claim 18, wherein the solution contains a single protease.

21. The applicator of claim 18, wherein the solution contains a plurality of proteases.

22. The applicator of claim 18, wherein the solution further contains an effective amount of at least one substance selected from the group consisting of: a local anesthetic, a coagulant and an anti-coagulant.

23. The applicator of claim 22, wherein the solution further contains an effective amount of an antibiotic.

24. The applicator of claim 9, further comprising a second reservoir that is operatively connected to the first reservoir, wherein the second reservoir is adapted for containing means capable of activating the at least one protease.

25. The applicator of claim 24, wherein the second reservoir is constructed from glass, metal or plastic.

26. The applicator of claim 24, wherein the first reservoir contains the protease solution wherein the at least one protease is substantially catalytically inactive and the second reservoir contains means for activating the at least one protease of the first reservoir.

27. The applicator of claim 9, wherein (a) the first reservoir contains the protease solution wherein the at least one protease is present in a substantially catalytically inactive form; and wherein the applicator further comprises; (b) a first receptacle for receiving the first reservoir; (c) a second reservoir containing a protease activating solution for activating catalytic activity of the at least one protease upon mixing with the first solution; (d) a second receptacle for receiving the second reservoir; and (e) a mixing chamber in fluid communication with the first and second reservoirs when received by the first and second receptacles, for mixing the first solution and the activating solution such that the at least one protease becomes catalytically active in solution.

28. The applicator of claim 27, wherein the mixing chamber includes a mixing mechanism for mixing the at least one protease and the activating solution such that the at least one protease becomes catalytically active in solution.

29. A method for treating a skin portion of a subject afflicted with a dermatological lesion, which comprises:
producing a solution containing an effective amount of at least one protease; and
directing the solution in the form of a stream into and out of contact with the skin portion such that the protease solution stream enzymatically and mechanically removes cells from the skin portion.

30. The method of claim 29, wherein the method further comprises: collecting the removed cells from the solution after streamed into contact with the skin portion.

31. The method of claim 29, wherein:
the stream is directed into contact with the skin portion via an inlet in a body member brought into contact with the skin to define a confined space with the skin communicating with the inlet via a first passageway through the body member; and
the solution stream, with the cells removed thereby from the skin portion, are directed away from the skin portion via an outlet from the body member communicating with the confined space via a second passageway through the body member.

32. The method of claim 31, wherein the open end of the body member is of a flexible plastic material effective to accommodate irregularities on the surface of the object to be treated and to seal the confined space.

33. The method of claim 32, wherein the body member is a housing having an open end mounting a head; and the flexible plastic material is in the form of a flexible skirt of plastic material carried by the head and formed with an annular rim to contact the surface of the skin portion to be treated; the head being threadedly mounted on the housing to permit axial adjustment of the distance between the annular rim of the skirt, and at least one of the passageways in order to accommodate irregularities in the skin portion to be treated.

34. The method of claim 33, wherein the flexible skirt is of conical configuration, and the annular rim is an out-turned rim to enhance its contact with the skin portion to be treated.

35. The method of claim 29, wherein at least one protease is selected from the group consisting of papain, bromelain, plasminogen activator, plasmin, mast cell protease, lysosomal hydrolase, streptokinase, pepsin, vibriolysin, krill protease, chymotrypsin, trypsin, collagenase, elastase, dipase, proteinase K, Clostridium multifunction protease and *Bacillus subtilis* protease.

36. The method of claim 29, wherein the solution contains a single protease.

37. The method of claim 29, wherein the solution contains a plurality of proteases.

38. The method of claim 29, wherein the solution further contains an effective amount of at least one substance selected from the group consisting of: a local anesthetic, a coagulant and an anti-coagulant.

39. The method of claim 29, wherein the solution further contains an effective amount of antibiotic.

40. The method of claim 29, wherein the at least one protease is activated shortly prior to the streaming of the protease solution over and in contact with, the skin portion.

41. The method of claim 40, wherein the at least one protease is activated by (a) maintaining the at least one protease at a first temperature in which the at least one protease is substantially catalytically inactive and then changing the first temperature to a second temperature at which the at least one protease is catalytically active; (b) providing the at least one protease in a powder form and mixing the powder with a solution to which the at least one protease becomes catalytically active; or (c) providing the at least one protease in a first solution in which the at least one protease in substantially catalytically inactive and mixing the first solution with a second solution so as to achieve a mixed solution in which the at least one protease is catalytically active.

42. The method of claim 41, wherein the mixed solution differs from the first solution by at least one parameter selected from the group consisting of pH, ion concentration, free metal concentration, hydrophilicity and hydrophobicity.

43. The method of claim 30, wherein collecting the removed cells is effected via filtration.

44. The method of claim 30, wherein collecting the removed cells is effected via continuous flow centrifugation.

* * * * *